United States Patent
Guerrieri et al.

(10) Patent No.: US 9,039,883 B2
(45) Date of Patent: May 26, 2015

(54) METHOD AND APPARATUS FOR MANIPULATING SINGLE CELLS AND SMALL AGGREGATES THEREOF

(75) Inventors: Roberto Guerrieri, Bologna (IT); Massimo Bocchi, Sasso Marconi (IT)

(73) Assignee: CELLPLY S.R.L., Bologna (IT)

( * ) Notice: Subject to any disclaimer, the term of this patent is extended or adjusted under 35 U.S.C. 154(b) by 1320 days.

(21) Appl. No.: 12/302,128

(22) PCT Filed: May 31, 2007

(86) PCT No.: PCT/IB2007/001427
§ 371 (c)(1),
(2), (4) Date: Nov. 24, 2008

(87) PCT Pub. No.: WO2007/138464
PCT Pub. Date: Dec. 6, 2007

(65) Prior Publication Data
US 2009/0288963 A1   Nov. 26, 2009

(30) Foreign Application Priority Data
May 31, 2006   (IT) .......................... MI2006A001063

(51) Int. Cl.
*B03C 5/02*    (2006.01)
*B03C 5/00*    (2006.01)

(52) U.S. Cl.
CPC ................. *B03C 5/005* (2013.01); *B03C 5/026* (2013.01)

(58) Field of Classification Search
CPC ............................................. B03C 5/00–5/028
USPC .......... 204/450–470, 600–621, 643, 644–674
See application file for complete search history.

(56) References Cited

U.S. PATENT DOCUMENTS

| | | | |
|---|---|---|---|
| 4,747,919 A * | 5/1988 | Anderson ..................... 204/455 |
| 5,814,668 A * | 9/1998 | Whittemore et al. ......... 514/625 |
| 6,932,893 B2 * | 8/2005 | Bech et al. ................ 204/403.01 |
| 7,189,578 B1 * | 3/2007 | Feng et al. ..................... 436/174 |
| 2002/0036139 A1 * | 3/2002 | Becker et al. ................ 204/450 |
| 2002/0053399 A1 * | 5/2002 | Soane et al. .................. 156/292 |
| 2002/0092767 A1 * | 7/2002 | Bjornson et al. ............. 204/451 |
| 2002/0125139 A1 * | 9/2002 | Chow et al. ................... 204/601 |
| 2002/0182627 A1 | 12/2002 | Wang et al. |
| 2004/0011652 A1 * | 1/2004 | Bressler ........................ 204/643 |
| 2005/0139473 A1 | 6/2005 | Washizu et al. |
| 2006/0196772 A1 * | 9/2006 | Kim et al. ..................... 204/547 |
| 2006/0231405 A1 * | 10/2006 | Hughes et al. ................ 204/547 |

FOREIGN PATENT DOCUMENTS

| | | |
|---|---|---|
| EP | 1088592 | 4/2001 |
| WO | 9962622 | 12/1999 |

* cited by examiner

*Primary Examiner* — Bach Dinh
(74) *Attorney, Agent, or Firm* — Faegre Baker Daniels LLP

(57) ABSTRACT

A well, in particular an open well (14) with an upper end having a vertical axis (101), for containing a liquid and particles contained within said liquid, characterized by comprising at least two manipulation electrodes (1, 2, 3, 31, 32, 36, 17, 40, 41) able to be powered by electrical voltages, in particular alternating electrical voltages, so as to manoeuvre particles within the well by means of the dielectrophoretic effect. A platform comprising a plurality of wells as described above and a method for using said well.

17 Claims, 21 Drawing Sheets

METHOD AND APPARATUS FOR MANIPULATING SINGLE CELLS AND SMALL AGGREGATES THEREOF

CROSS REFERENCE TO RELATED APPLICATIONS

This application is the U.S. national phase of PCT/IB2007/001427 filed May 31, 2007, which claims priority of Italian patent application No. MI2006A001063 filed May 31, 2006.

FIELD OF THE INVENTION

The present invention concerns techniques for selecting and modifying particles such as single cells, microorganisms and small aggregates thereof. The field of application of this methodology and the relative apparatus can be in the biotechnology field, for example for monitoring the outcome of interactions between cells, including in the presence of different chemical compounds; in the medical field, for example for determining how the immune system reacts to the introduction of new stimuli to cells in charge of immune control; in the industrial biology field, in that the method and apparatus of the present invention enable cells and bacteria to be modified and a selection to be made therefrom so that those of greatest industrial interest can be extracted from a large number of specimens.

STATE OF THE ART

The conventional support available to those undertaking very small-scale biological or chemical experiments is the multi-well plate, also known as microtiter. Each well on these platforms can host chemical and biological material, but has no active function for the purpose of manipulation integrated therein. The number of wells simultaneously present on one plate can currently exceed one thousand. The capacity to intervene in an active manner on biological material, for example single cells or cell aggregates, has become an increasingly felt need in the fields of the aforementioned applications. To achieve these results a few solutions are currently available.

Implementation of platforms with large numbers of wells usable in parallel is described in U.S. Pat. No. 6,716,629: "Apparatus for assay, synthesis and storage, and methods of manufacture, use and manipulation thereof", which explains how the micro-well design can be optimized by a suitable selection of materials and the relative surfaces which characterize them. The absence of sensors and actuators integrated therein renders them uncompetitive with the arrangement presented herein.

The creation of wells aimed at measuring developments in the material contained therein was proposed among others by Caillat et al. in EP1390467A1 "Use of a miniature device for separating and isolating biological objects and methods used". This document teaches to produce wells in which material is inserted and maintained analysed by measurement electrodes. There are many limitations to this arrangement: the displacement of particles contained in the wells cannot be controlled, and so objects of moderate size such as cells cannot be controlled, with measurements being restricted to macroscopic type. The problem derives inter alia from the possibility that cells deposited in the wells are located in regions where measurements and analyses cannot be carried out. Even more so, the device does not allow single cells to be forced into such a position as to ensure their contact. Unfortunately, cellular interactions of immunological interest are mediated by the contact between cell walls, rendering this type of study impossible. Also, the closed at a lower end does not allow the supernatant where the cells grow to be changed, in order to remove, for example, metabolic residues. Finally the device does not allow the voltages necessary to enable electroporation and electrofusion effects to be applied.

The manipulation of particles within a fluid can be dealt with by dielectrophoresis as proposed in U.S. Pat. No. 6,610,188: "Electrode array for field cages". In this document an electrode configuration is proposed which has particular qualities, in terms of the electric field generated for the formation of dielectrophoretic cages. This arrangement has various disadvantages: 1) the electrode configuration is complex and requires alignment procedures for their manufacture, hence increasing costs and reducing yields; 2) the cages are conceived as closed structures, which prevents the supernatant in which the particles are found to be modified, or as field formations which are created within a fluid flow. In this latter case it is impossible to study the interactions of particles which have to remain in contact with each other; 3) the measurement procedure does not have the advantage of being able to suitably move the particles. The document proposes various schemes for measuring impedance of the characteristics of the materials contained in the fluids. With regard to measuring the cell properties by impedance variation, reference can be made to the work: "Capacitance cytometry: measuring biological cells one by one", PNAS, vol 97, 10687-10690, 2000. This work demonstrates that changes in capacitance induced by the presence of single cells can be measured. The need to combine impedance measurements with the controlled motion of the analysed material remains however unfulfilled; this deficiency severely affects the quality of the measurement.

In U.S. Pat. No. 6,942,776 "Method and apparatus for the manipulation of particles by means of dielectrophoresis", G. Medoro proposes an electronic platform able to create traps which can capture and even displace particles trapped within them, as well as measure their characteristics by means of embedded sensors. This method integrates in a single platform both the entrapment and subsequent manipulation of cells or particles in general. The disadvantage of this technology is related to the need to create a closed chamber in which the entrapment processes take place. This makes it difficult to oxygenate the cells trapped within. In addition the chamber does not allow the composition of the fluid in which the particle is located to be modified at the discretion of the researcher, if not by changing it in the chamber as a whole. Finally, the single chamber structure presents a limited number of entrance channels which does not allow an adequate facility for intervention on the content of the space in which the chemical or biological reaction of interest takes place.

Developments in biological tissue in the presence of drugs or other compounds was dealt with in Thielecke et al. "A Multicellular Spheroid-Based Sensor for Anti-Cancer Therapeutics", Biosens. Bioelectron., 2001, 16, 261-9. This work shows that developments in a small sample of organic tissue can be monitored, hence demonstrating phenomena useful from the diagnostic and therapeutic viewpoint. However, the microfluid system used is rather complex and does not allow cell-cell interaction due to the fact that control of position is not adequate for the purpose. The methodology cannot be scaled up to the required level for applications where tests on a large number of parallel samples are required, but a few dozen samples in parallel can be managed at the cost of great effort. in optimizing the fluid system.

Also desirable would be the ability to carry, out procedures to modify the genetic material of microorganisms, for example by electroporation inside wells or the fusion of 2 or more cells which can hence share their genetic material. Single cell electroporation is a process that is attracting considerable interest due to the need to modify cellular and bacterial DNA by introducing new genetic material therein. By way of example only, the work "A microchip for electroporation of primary endothelial cells" Sensors and Actuators, A, Vol 108, 2003 pp 12-19, describes a possible insertion of DNA into eukaryotic cells. This technique is particularly interesting because of the efficiency of the process, measured in terms of effectively mutated cells, and survival of cells. This patent extends the state of the art of cell electroporation by the ability to position multitudes of single cells in front of the electrode which permeabilises them. In addition, of particular importance for more sophisticated protocols, this patent teaches how to fuse several microorganisms in a controlled manner. The importance of controlled single cell fusion and methods for its attainment are taught in patent application U.S. Pat. No. 7,018,819 B2 which demonstrates apparatus able to bring into contact single cell pairs and apply suitable voltages to them with the aim of fusing them. The demonstrated technology requires a particularly complex positioning of the cells which cannot be scaled up to groups of cells, as is required for applications and as made possible by the descriptions in this document.

SUMMARY OF THE INVENTION

The problems identified above have been resolved in the present invention by a well, in particular a micro-well suitable for the manipulation of and/or measurements on materials, in particular biological material, such as particles (a term which includes cells, microorganisms, their aggregates, fragments and other types of material, including liposomes) suspended in a liquid contained within the well, a platform comprising several wells, and methods in which wells and platforms are used in accordance with the independent claims attached.

A particular of the invention is defined by the contents of the dependent claims attached.

The well of the present invention is able to contain biological material and to change the supernatant in which the particles are immersed by drawing from one or more sources of liquid, by means of a suitable system of channels; within the well a group of electrodes is located having the function of displacing with precision individual or small groups of particles so as to bring them into mutual contact, for example by locating them in front of other electrodes that measure the variation in impedance resulting from the presence of particles which are moved in front of the measurement electrodes. The electrodes, in particular the measurement electrodes, can also apply relatively higher voltages so as to induce particular phenomena of interest, such as electroporation and cellular fusion.

BRIEF DESCRIPTION OF THE FIGURES

FIG. 1b: is a view from above, on the section B-B', of the electrode 1 of FIG. 1a.

FIG. 1c: is a view from above, on the section C-C', of the electrode 2 of FIG. 1a.

FIG. 1d: is a view from above, on the section D-D', of the electrode 3 of FIG. 1a.

FIG. 4b: is a view from above, on the section B-B', of the electrode, 31 of FIG. 4a.

FIG. 4c: is a view from above, on the section D-D', of the electrode 32 of FIG. 4a.

FIG. 8b: is a view from above, on the section B-B', of the electrode 33 of FIG. 8a.

FIG. 10b: is a view from above, on the section B-B', of the electrodes 36 and 37 of FIG. 10a.

FIG. 10c: is a view from above, on the section C-C' of FIG. 10a, of the electrodes 38 and 39, in particular but not exclusively, measurement electrodes which can be present in the embodiment in FIG. 10a.

FIG. 10d: is a view from above, on the section D-D', of the electrodes 40 and 41 of FIG. 10a.

FIG. 13: shows the alignment of two particles 22 and 23 subjected to negative electrophoresis once inserted into the well having the structure described in FIG. 10a.

DETAILED DESCRIPTION OF THE PREFERRED EMBODIMENTS OF THE INVENTION

Figure 1A:
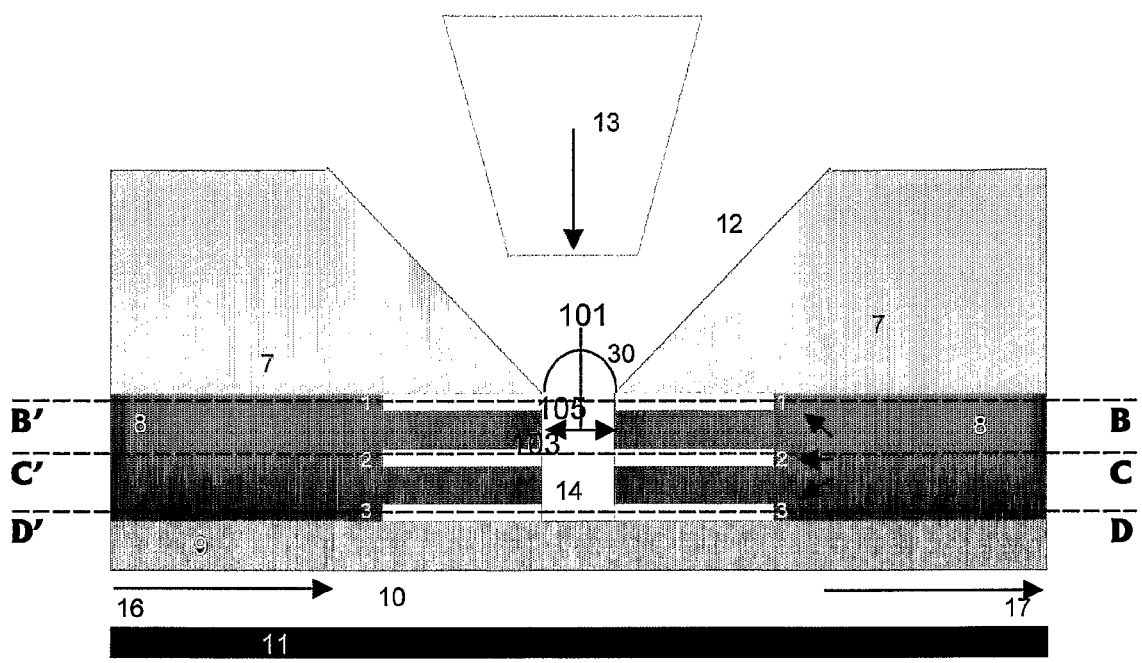
FIG. 1a: shows a section, indicated by A-A' in the following figures from 1b to 1d, through a well according to one embodiment of the present invention, in the configuration with 3 annular electrodes.

The functional selection of cells is a key point in immunological and biotechnological investigations. Interest in this problem derives from the fact that cells can be selected both in terms of their biochemical characteristics, such as the presence of special membrane receptors, or based on their behaviour in particular situations of interest. In this latter case, selection does not require complex preliminary characterization, but only a precise definition of the desired characteristics. The problem of functional selection is also a key step in the "direct evolution" procedure for generating microorganisms which have desirable characteristics. This approach is based on the capacity for introducing modifications to the genetic material of a microorganism in a substantially random manner, then selecting among the different specimens thus generated those that are functionally more promising. Typical selection parameters include for example the ability to live in environments with a different pH value than normal. In this case, selection can take place simply by slowly changing the pH and seeing which microorganisms survive. A more complex situation is one in which selection cannot be achieved simply by destroying non-surviving microorganisms. By way of example, the capacity of a microorganism to produce a substance of interest requires a measurement thereof. The apparatus proposed herein enables selections to be made which make measurable parameters determinable by impedance variations, or which combine the ability to move single cells in parallel wells, by means of dielectrophoresis, particularly negative dielectrophoresis (DEP), with other known analytical methods which will be discussed later. The device according to the present invention can be used to carry out different functions, to be listed and described hereinafter.

In order to facilitate understanding of the apparatus described, there follows a description of the principle of operation of the apparatus for enabling the motion of particles, also known as actuation, which utilizes the principle of dielectrophoresis. Since the invention is achievable in different ways, thus enabling different compromises between flexibility and ease of production to be gained, discussion will start from the simplest and proceed to the most complex implementations.

In general electric fields which vary in space create dielectrophoretic effects within the liquid. In particular for phenomena of interest, electrophoretic effects act as a force which pushes the particles towards regions of lower electric field intensity. This phenomenon is called negative dielectrophoresis and is of particular importance when high conductivity solutions are employed, such as physiological solution. In general, when the particles or cells of interest are heavier than water, this force can, inter alia, counteract the tendency for the particles to sink. For example by balancing dielectrophoretic with gravitational forces, the particle can be trapped in a well defined region of the well.

Structure and Operation of the System

With reference to FIG. 1a, a section is shown, indicated as A-A' in the subsequent figures, of a well 14 in accordance with the present invention. Firstly, a nozzle 13 can be seen, arranged to deposit fluid droplets containing the material of interest. This nozzle can form part of an apparatus able to deposit single cells or particles. Such apparatuses are known in the field of single cell deposition; commercial products exist which allow liquid droplets to be deposited within which the presence of even a single cell or particle of the desired type can be ensured. These deposition systems for biological material are commercially supplied for example by DakoCytomation and Becton Dickinson and are able to deposit material which is withdrawn from different containers, therefore enabling different cells and/or particles to be present in the same site. The deposition can be achieved with a geometric precision of the order of a few microns.

The apparatus is able to deposit material inside the well 14. The internal wall 103 which delimits the well 12 is of a suitable material; it is preferably hydrophilic if the liquid to be introduced into the well is aqueous, hydrophobic if the liquid is lipidic. Within the well, formed of dielectric material 8, the electrodes 1, 2 and 3 face each other. These electrodes are able to apply suitable potentials, preferably time variable potentials, to the liquid inside the well. The well, in accordance with a particular embodiment of the inventions can be connected at a lower end to a channel 10 and be of the open or semi-closed type. In this latter case, a semipermeable membrane 9 separates the well from the underlying fluid which can be made to flow by virtue of the pressure difference applied to the ends of the channel 10. The semipermeable membrane can instead be absent if the well is of the open type. The channel 10 can also be produced from bio-compatible and, in accordance with a possible embodiment of the invention, transparent material. The channel 10 can be associated with a single row of wells or an assembly of rows if the wells are part of a platform or microtiter whereby the wells are matrix organized. The material used in the channel 10 should be hydrophilic or hydrophobic to facilitate liquid passage, and so has walls that are preferably of the same characteristic as the internal wall 103 of the well. If the base 11 of the structure is transparent, lighting applied to the base of the device allows the contents of the well to be illuminated. This characteristic can be maintained even in the presence of a semipermeable membrane.

Figure 2:
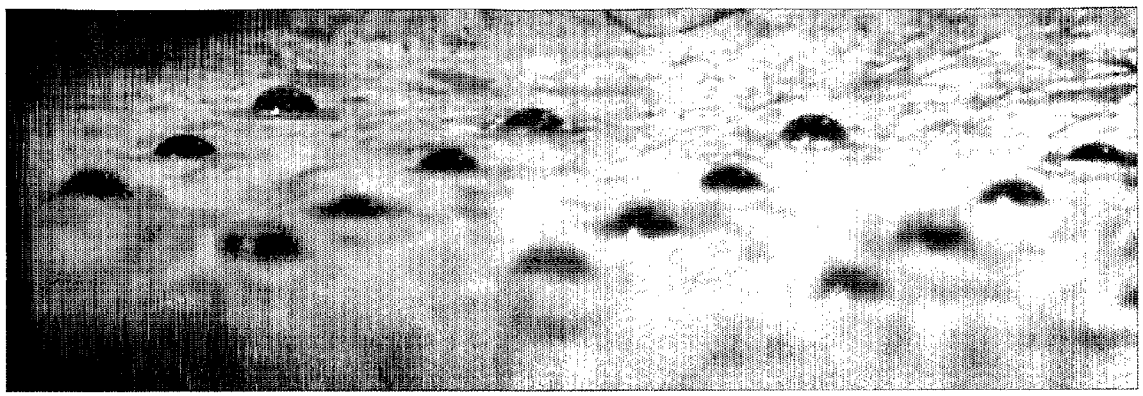
FIG. 2: shows the image of an array of wells filled with a fluid, and the formation of a meniscus consequent on hydrophobic treatment of the surface.
Figure 18:
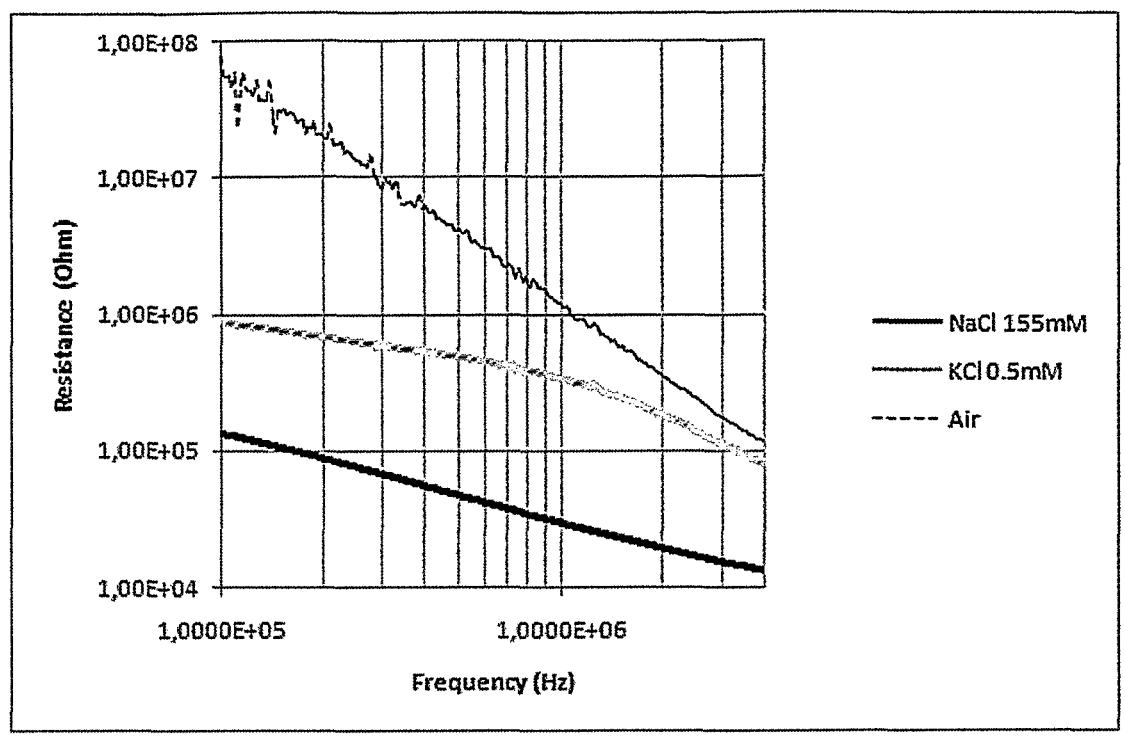
FIG. 18: variation of the impedance measured during substitution of the supernatant.

The channels 10 can be used to fill themselves and the wells 14 afferent to them. A typical embodiment of said channels is shown in FIG. 18. The channels 10 are subject, when necessary, to a slight pressure difference between their inlets 16 and their outlets 17. This pressure difference results in flow of fluid and the consequent transportation of material from the inlets 16 to the wells 14 and from the wells 14 to the outlets 17. As can be seen in FIG. 1a, the wells have a suitably hydrophilic or hydrophobic interior surface and so the liquid is pushed upwards by capillary action until it reaches the upper edge 105 of the useful space, intended to contain the well liquid. In accordance with a preferred embodiment, the well, which can be for example cylindrical, comprises an upper part, having walls 12 preferably of opposite characteristics to those of the internal wall 103 delimiting the well (i.e. the wall delimiting the space for containing the liquid), i.e. being hydrophobic if the internal wall has hydrophilic characteristics and vice-versa. The upper part has walls preferably with a cross-section which widens starting from the internal wall of the well, and can have a conical form if the well, in the part which receives the liquid, has a cylindrical form. The liquid level stabilizes in that the surface 12 of the upper part has the aforesaid characteristics. According to a possible embodiment, it suffices that the walls external to the well, adjacent to the internal wall, have a nature that is opposite to that of the latter, even in the absence of the aforedescribed increasing section part. This effect is illustrated in FIG. 2, showing a photograph of an array of wells, each of which displays the formation of a meniscus by virtue of the hydrophobic treatment of the surface external to the wells which contain aqueous liquid and have a hydrophilic internal wall. In the entire description that follows, for simplicity it is assumed that the liquid of interest is of aqueous type with suitable compounds dissolved therein if required. Should the liquid be lipidic in nature, it is intended that the characteristics of the surfaces in the interior of the well 14 and external thereto 12 are respectively hydrophobic and hydrophilic.

When a well is full, potentials can be applied to the electrodes 1, 2 and 3 located in the well in order to achieve the required performance.

The need to execute many parallel operations on many wells can require them to be formed in an ordered manner on a normal platform, or microtiter. A preferred embodiment of a well assembly is that of a two-dimensional array in which the wells are organized by rows and columns. Independently of the manner in which they are activated, as will be explained in detail to follow, the generic well can unequivocally be identified by designating a pair of codes which identify the row and column to which it belongs.

Figure 3:
FIG. 3: shows the image of a well filled with liquid in an inverted position (upside down) and the accumulation of cells at the air-liquid interface.

The apparatus of this patent is also suitable for allowing the growth of cell lines in the previously described wells. The cell lines can be grown from cells deposited in a well and treated therein. Often it is not appropriate to subject cells to an electric field for long periods, and so a possible embodiment of the invention comprises a semipermeable membrane 9 which prevents the cells from falling into the channel 10 when the applied voltages are removed. With this solution the downflow of cells through the channels is prevented and the cells must be removed from the wells themselves by suction; it is also possible that the particles, particularly in the case of cells or microorganisms, adhere to the membrane 9. In accordance with a different embodiment of the invention, a semipermeable membrane is not provided, and the well base opens directly into the channel 10. If required, said solution also enables cells to be discharged and withdrawn through the channel. The invention also concerns a method for using wells or platforms which comprises use of the system in two different configurations which we shall call direct and inverted. The first configuration is the one just described and is used only for the steps of manipulation, loading and/or measurement to be carried out in the wells. The second configuration proposes that the entire apparatus be inverted, placing the wells with downward facing apertures. In the case of cells heavier than water, the cells deposit on the air-liquid surface and remain there without requiring a membrane to retain them. In this case, a further inversion of the apparatus returns it to the original configuration. This manner of operation is shown in FIG. 3 where the image of a well filled with aqueous liquid is shown in the inverted position, the liquid not descending because of the hydrophobicity of the external surface 12. Dark stains are also visible representing K562 cells which lie on the air-water surface.

It is clear that in the inverted configuration, that which was defined as the upper open end of the well is found in the lower position, however it is always designated in the same manner for simplicity. This is also obviously true for the term "lower". This method is particularly suitable in the case of wells of the present invention for which the manipulation electrodes can be powered in the direct configuration for suitably suspending the particles, while in the inverted configuration the generation of electric fields can be suspended, so avoiding stresses potentially dangerous to them, especially if dealing with cells or organisms, without the particles falling into the channel in the absence of the membrane, or adhering thereto if present, or adhering to other surfaces.

The well can be produced for example as follows: a layer of dielectric material 8 having a thickness which can vary for example from 1 micron to a few hundred microns and made with materials commonly used in the microsystems industry, such as Polyimide, Kapton or Pyralux, separates the electrodes consisting of conducting sheets 1, 2 and 3 made preferably from bio-compatible metals, such as gold or aluminium having a thickness in the order of a few microns or a fraction thereof equal to a certain percentage of the well depth. These metal layers can in their turn be covered with other materials which render them hydrophobic where required as, for example on the upper electrode 1, in particular ignoring the initially described further upper part. In this structure through-holes are opened, intended to form the actual well, suitable for receiving the liquid; the walls of the hole can be treated to give the required hydrophilic characteristics.

The through-holes for forming the wells 14, of suitable diameter, can be opened by common boring techniques, for example mechanical or laser. The diameter of the wells, for the applications of interest, in accordance with a possible embodiment of the invention can vary between 30 and 150 µm, preferably between 50 and 100 µm. The aperture in the upper part, conical or pyramidal or of suitable shape, as required, can also be produced by known methods such as mechanical boring or powder blasting. It is formed in an upper layer 7, also of suitable dielectric material, for example silicon, then treated, if considered appropriate, to confer hydrophobic behaviour to the mesh-like walls. If the material is silicon, the hole with the wall 12 can also be opened by anisotropic etching, particularly if a pyramid form is required. The entire well can also: be obtained by powder blasting. The fabrication method described above is particularly suited to the fabrication of platforms, so reducing or eliminating alignment problems. For example a dielectric layer 8 can be formed with embedded conducting plates intended to form the electrodes or groups of electrodes connected together (they can be continuous plates which involve all the wells, or strips which relate to one column or one row of wells in a matrix structure, or strips can be provided at different levels relative to a series of electrodes to be connected together and connected thereto by means of vertical contacts (108 in FIG. 15) to avoid contacts between different arrays, so ensuring the necessary connections, especially in matrix organizations), and then proceeding to hole boring. In accordance with a possible embodiment, a complete structure can be formed for the dielectric 8 with the conducting plates and the upper layer 7, and then proceed to boring holes with one or more different techniques as considered appropriate. Otherwise the dielectric 8 and the layer 7 with holes can be formed separately then coupled in a suitable manner, which however requires precise alignment. The production of this device is very simple as it does not require any alignment between the different planes, and in particular between the electrodes which are created together by the boring operation. This is highlighted in FIGS. 1*b*, 1*c* and 1*d* which show, respectively, sections B-B', C-C' and D-D' defined in FIG. 1*a*, from which the form of the electrodes 1, 2 and 3 can be noted.

Different embodiments of the well of the invention are possible, described hereinafter with reference to the figures. Regarding the construction and other characteristics, reference can be made to the aforedescribed with regard to the embodiment of FIGS. 1*a*, 1*b*, 1*c* and 1*d*.

Figure 4A:
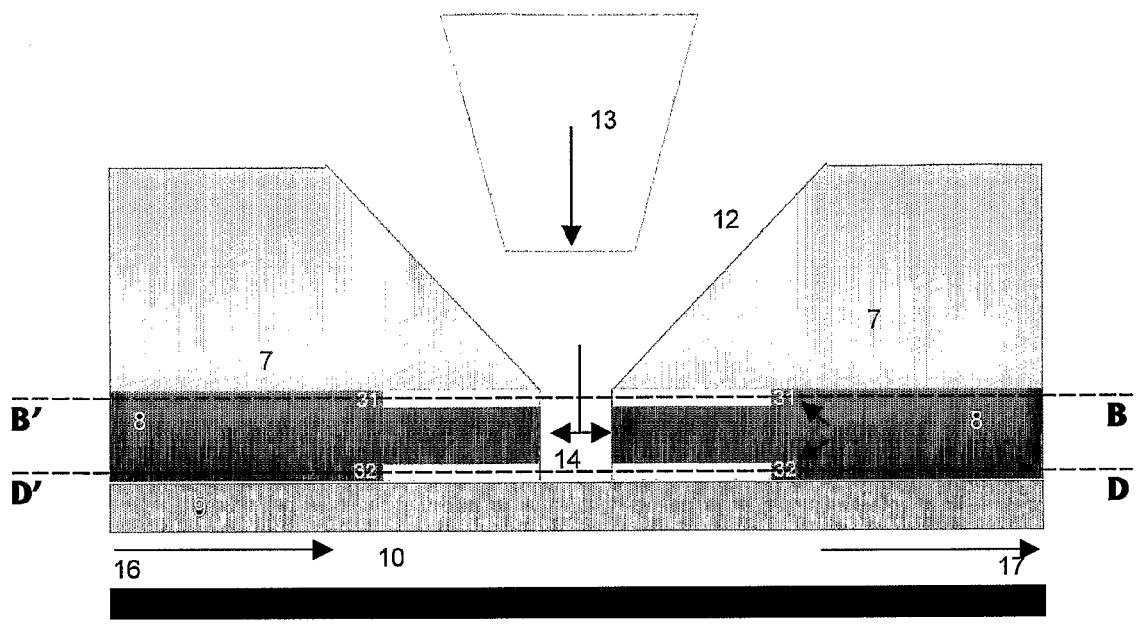
FIG. 4a: shows a section, indicated by A-A in the following FIGS. 4b and 4c, through a well according to one embodiment of the present invention, in the configuration with 2 annular electrodes.
Figure 4B:
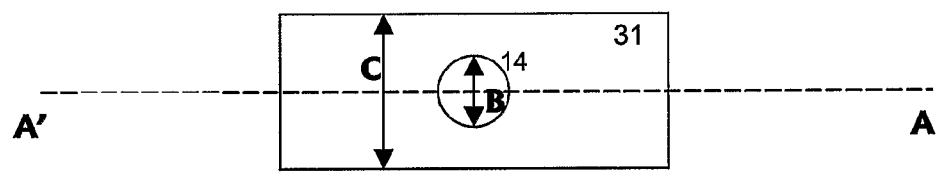
Figure 4C:
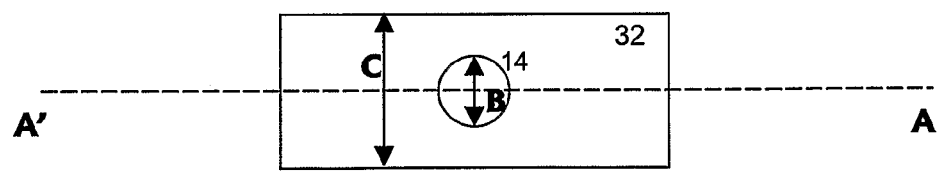

A simpler variant is described in FIG. 4*a* where only electrodes 31 and 32 are present.

Figure 5:
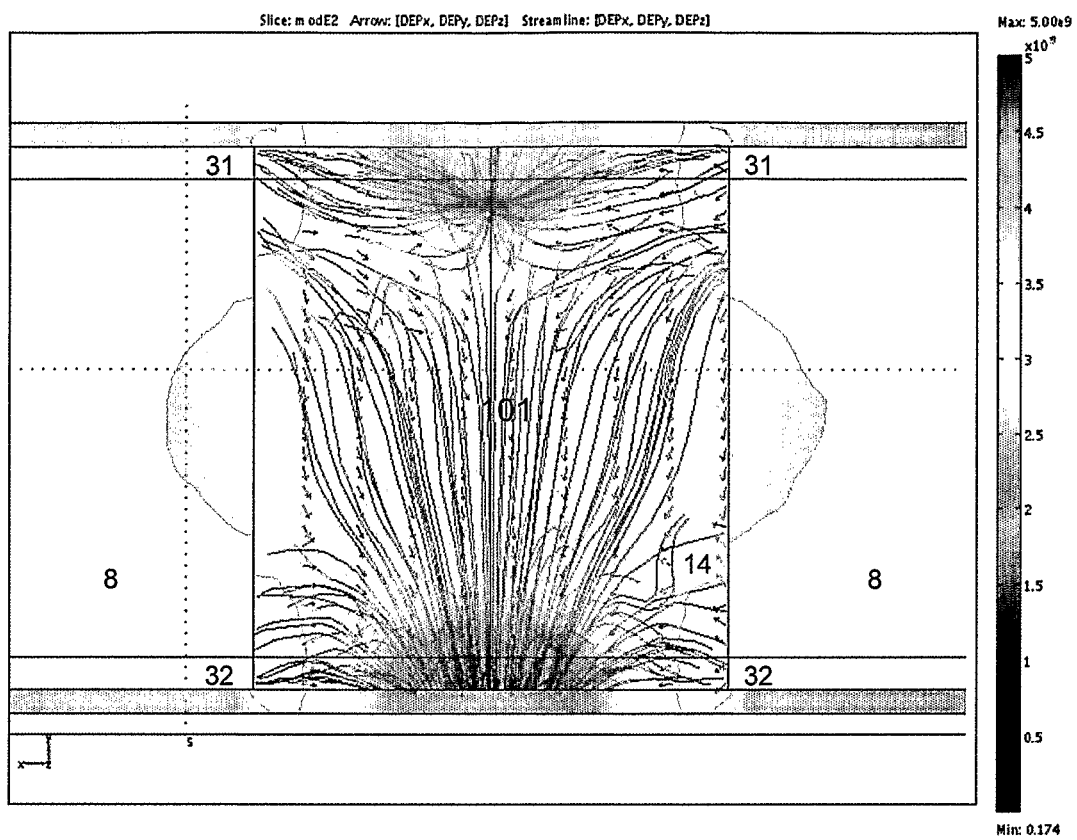
FIG. 5: shows the distribution of the electric field modulus along the section A-A' of a well having the structure with 2 annular electrodes described in FIG. 4. The potentials applied to the electrodes 31 and 32 are sinusoidal with the same amplitude, displaced in phase by 180 degrees.
Figure 6:
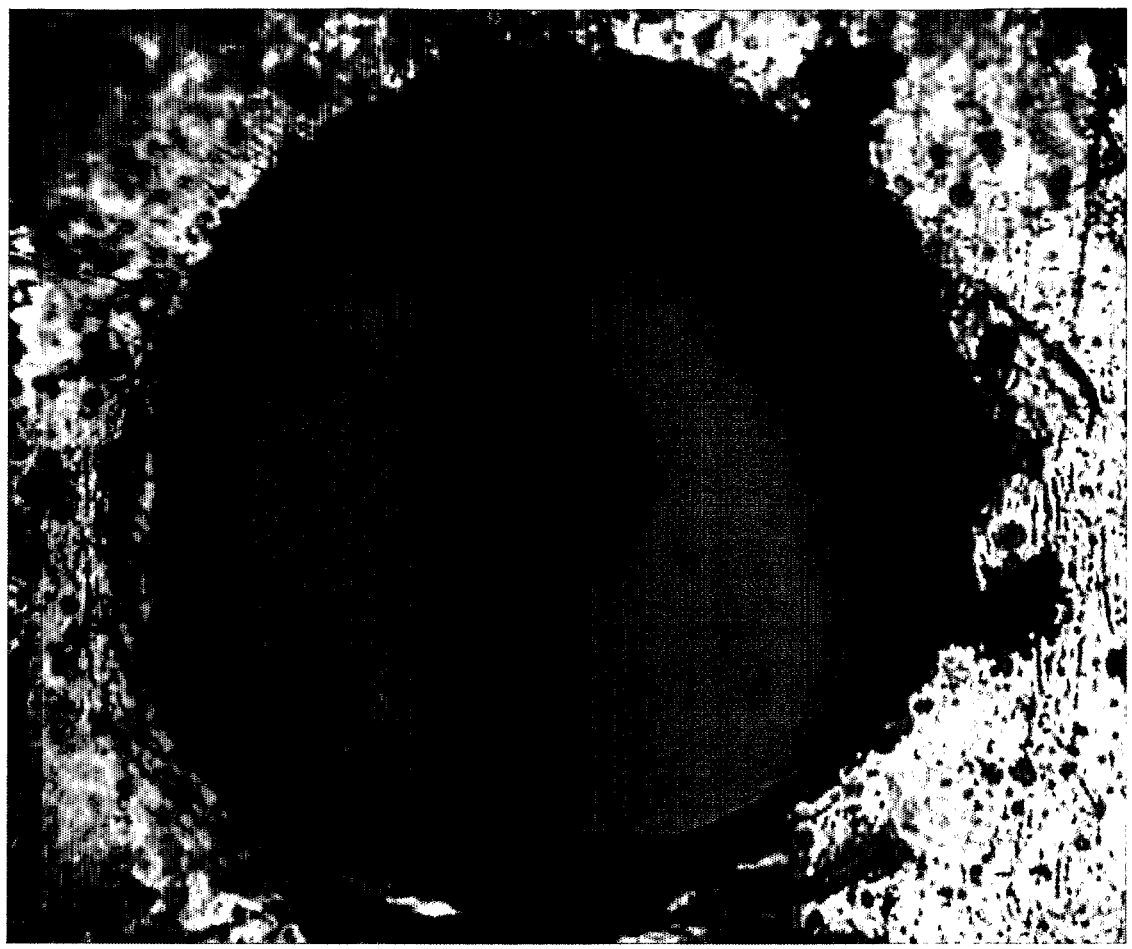
FIG. 6: shows the image of a polystyrene sphere with diameter of 90 micron inserted into a well with diameter of 300 micron and having the construction described in FIG. 4. By applying sinusoidal polarization voltages with amplitude of 15V peak-peak, the sphere is maintained in the minimum region represented in FIG. 5. In the absence of polarization voltages the sphere would fall as it is heavier than water.

If a sinusoidal voltage is applied to the lower electrode 32 and a zero or even a sinusoidal voltage of opposite phase to the other is applied to the upper electrode 31, a field configuration is obtained which shows two minimums located respectively in the central region of the two electrodes as shown in FIG. 5 which illustrates, in various colours, the distribution of the electric field modulus. The field configuration is easily explained by observing that 1) the electric field along the central axis of symmetry 101 has zero components perpendicular to the axis itself; 2) between the two electrodes there is a field component imposed by the potential; 3) in the regions contained between the two electrodes, the thickness of these latter has an important role in diminishing the size of the field perpendicular to the axis of symmetry. Under these conditions, the regions between the electrodes benefit from a situation such as to diminish the electric field modulus and in particular to create a minimum with respect to adjacent regions. An example of this type of operation is shown in FIG. 6, where a polystyrene sphere having a diameter of 90 micron is maintained in the previously described minimum region in a hole having a diameter of 300 micron with application of voltages of 15V peak-peak. In the absence of polarization voltages the sphere would fall as it is heavier than water. The arrows in FIG. 5 show the resultant direction of the forces acting on a particle, which take account of negative electrophoresis and gravity. The minimum, positioned at the upper electrode, is particularly suited for use as a potential cage for suspending and trapping particles, while the lower minimum is open towards the base of the well, enabling particles to fall.

Figure 1B:
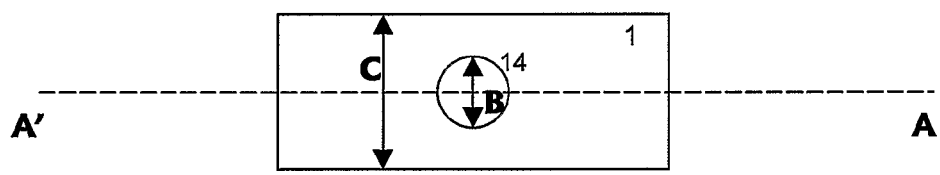
Figure 1C:
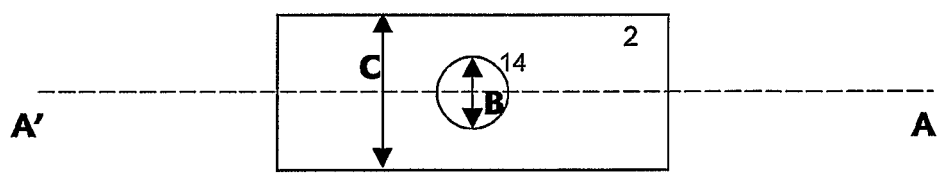
Figure 1D:
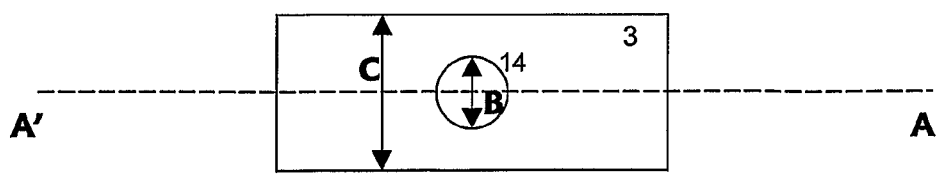

A slightly more complex actuator configuration is that of FIG. 1*a*. In this case a level of dielectric and metal has been added to the previously described structure. Electrodes 1, 2 and 3 are formed without requirements regarding their alignment. Their structure is shown in FIGS. 1*b*, 1*c* and 1*d* which represent, respectively, sections B-B', C-C' and D-D' defined in FIG. 1*a*. It is assumed for the moment that the upper electrode 1 and the lower electrode 3 are polarized by a sinusoidal voltage while the central electrode 2 is polarized by a sinusoidal voltage. in counterphase. Under these conditions, analysis shows that there is another, very pronounced, electric field minimum positioned in the central region of the intermediate electrode. Under these conditions, a field configuration can be created that traps particles which can be controlled in negative dielectrophoresis.

Figure 7:
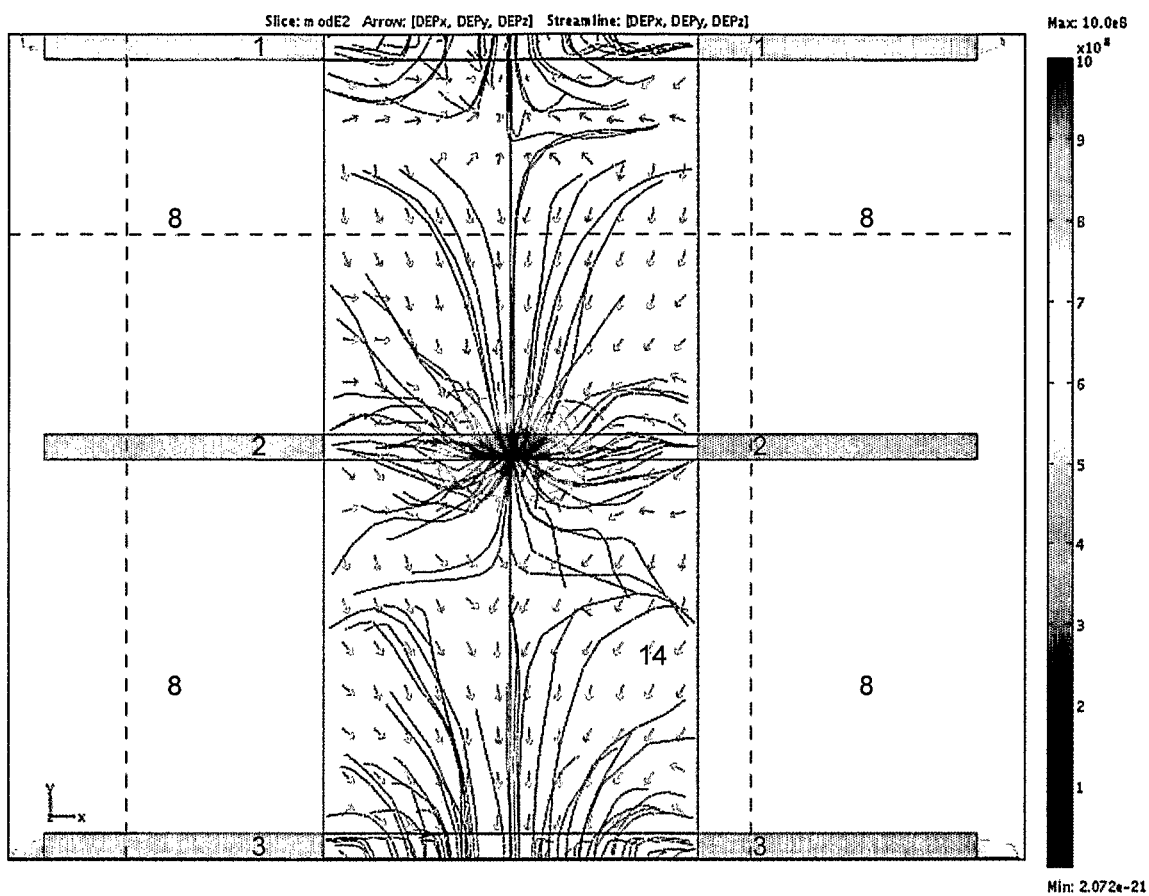
FIG. 7: shows the distribution of the electric field modulus along the section A-A' of a well having the structure with 3 annular electrodes described in FIG. 1. The potentials applied to the electrodes 1, 2 and 3 are sinusoidal with the same amplitude, in phase with the electrodes 1 and 3 and displaced in phase by 180 degrees compared to the voltage applied to electrode 2.

In contrast to the preceding case, the central minimum is enclosed by a at a lower end and upperly closed cage. The field configuration obtained from numerical simulations is shown in FIG. 7. Other schemes for powering the electrodes can lead to the same results, for example keeping the central electrode in zero voltage and powering the others with twice the voltage.

The introduction of a particle requires, in accordance with a possible operative method, the following steps: 1) the upper electrode and the central electrode are powered by an equal voltage and in counterphase with the lower electrode; during this step, a particle can be introduced which, if heavier than water, sinks down to the field minimum which is found near the intermediate electrode; 2) inversion of voltage phase applied to the upper electrode; this change has two effects: it "closes" the cage created close to the central electrode and creates a sort of stopper for the structure, preventing any emissions of further particles which, if emitted, would be captured by the minimum created by the upper electrode.

Should a semipermeable membrane not be present, release of the particle from well 14 can be achieved simply by removing the potentials applied by the electrodes. In this situation the particle leaves the well 14 by gravity, into the channel 10 if present. This approach is typically employed for the release of all the particles contained in the wells. In the following will be described targeting techniques in matrix format which allow selective release of the particles in the wells of interest.

If the manipulated particles have biological relevance, it is appropriate that all the applied voltages, in opposition to each other, have a mean value of zero to reduce the risk of producing damage, reducing the maximum values of the field to which the particle is subjected.

The preceding structures allow electric field configurations to be created which block the particles along the central axis of symmetry of the well. This has the advantage of avoiding adhesion of particles to the wall. In some cases it is appropriate to create field configurations able to trap the particles in a region near to a predefined electrode and in a predictable configuration.

The wells in accordance with the embodiments described hereinafter, have the characteristic of entrapping the particles in a well defined region, for example, close to a reference electrode.

Figure 8A:
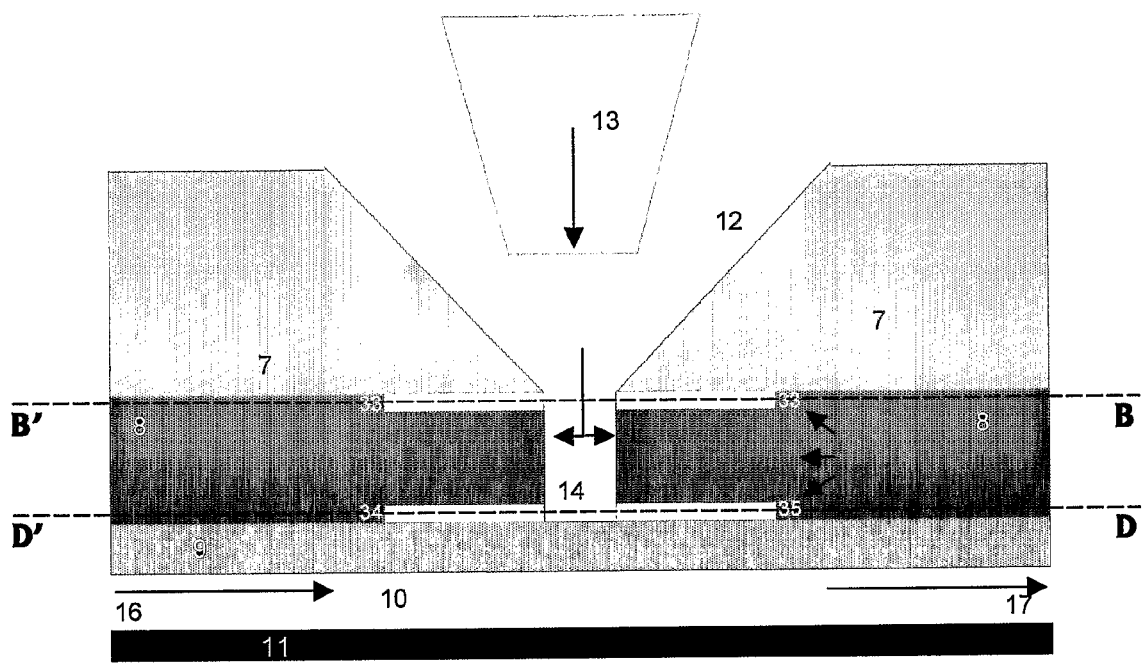
FIG. 8a: shows a section, indicated by A-A' in the following FIGS. 8b and 8c, through a well according to a further embodiment of the present invention, in the configuration with 2 opposing horseshoe electrodes and an annular electrode.
Figure 8B:
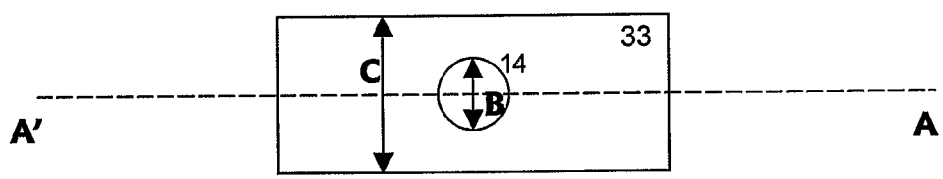
Figure 8C:
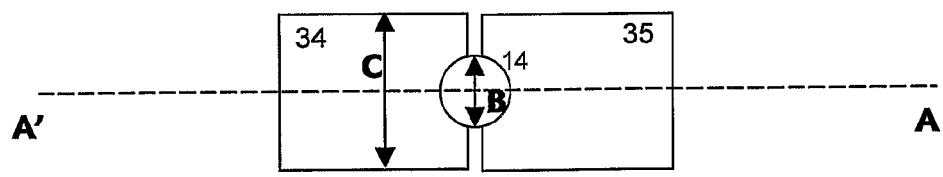
FIG. 8c: is a view from above, on the section D-D', of the electrodes 34 and 35 of FIG. 8a, of horseshoe configuration and physically separated. In this case the electrodes can be maintained at different potentials.

Reference is now made to a structure formed by interposing a layer of dielectric material between two metal layers which form electrodes as shown in FIG. 8*a*. The electrodes 34 and 35 can be formed as coplanar plates, facing the internal wall of the well, each forming a rim which is a portion of the perimeter of the well cross-section; the rims are symmetrically disposed with respect to the well. The formation of this structure is simple as it does not require any alignment between the upper electrode 33, inferior electrodes 34 and 35 and the well 14, the structure being constructed in a similar manner to that described above. The only required alignment is that needed between the well 14 and the region that separates the electrodes 34 and 35 as shown in FIG. 8*c* which represents the section D-D' defined in FIG. 8*a*. The upper electrode 33 is formed as described in FIG. 8*b* which represents the section B-B' defined in FIG. 8*a*.

By applying a sinusoidal voltage to the contacts 34 and 35, setting the voltage at the same amplitude and with a phase difference of 180 degrees, and keeping the contact 33 earthed, the electric field obtained has a distribution of the following type:

1. in the annular region between the contacts 34 and 35, the field modulus has a very high value where the contacts are close and tends to fall off in the central region due to the distance between the electrodes;
2. in the annular region within the electrode 33 the field modulus is very small due to the proximity of the contact;
3. in the cylindrical region 14, the field modulus is greatest near the lateral surfaces and decreases moving towards the centre of the structure.

Figure 9:
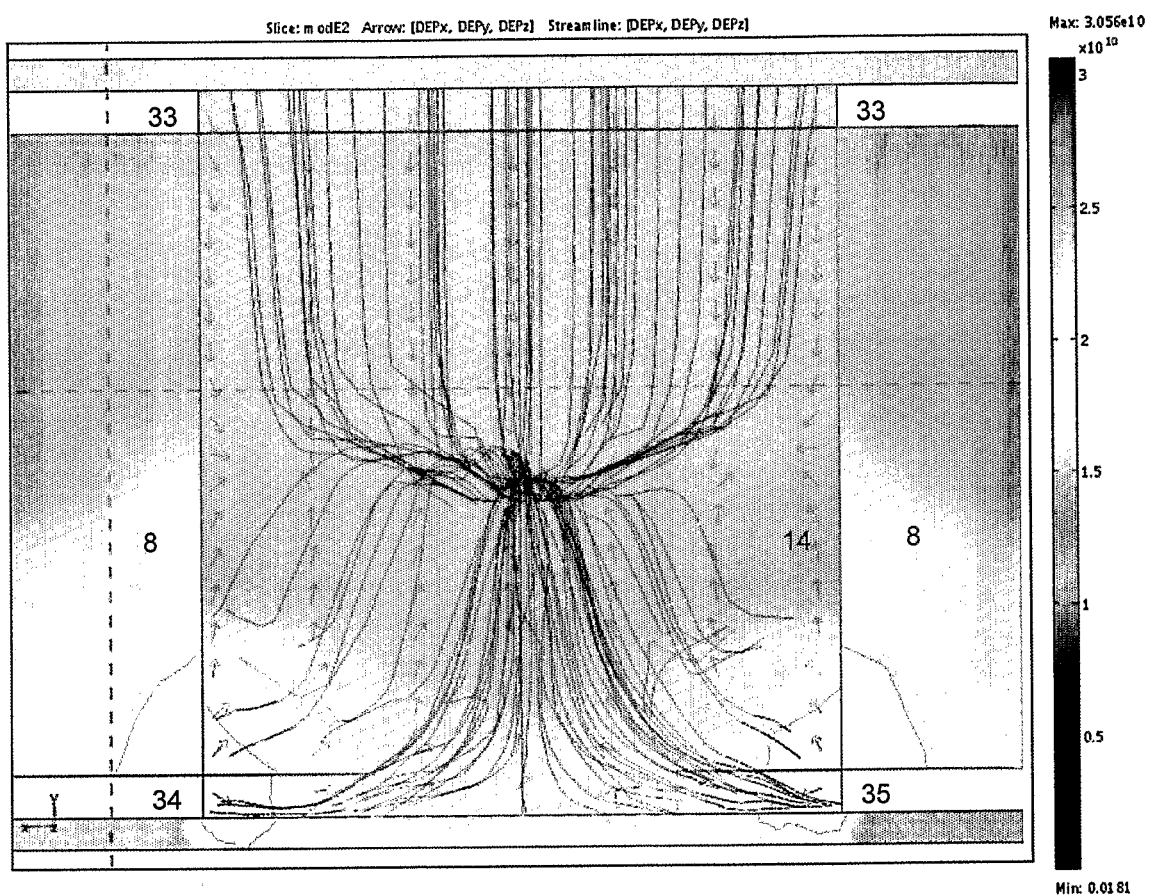
FIG. 9: shows the distribution of the electric field modulus along the section A-A' of a well having the structure described in FIG. 8. The potentials applied to the electrodes 34 and 35 are sinusoidal with the same amplitude, displaced in phase by 180 degrees while the contact 33 is maintained at earth.

An electric field modulus gradient is hence created as shown in FIG. 9. In this manner a dielectrophoretic field is created which exerts a direct force from the electrodes 34-35 towards the electrode 33 and a force able to counteract that of gravity. A characteristic of this force field is that it propels the particles into a region of low field intensity situated near the wall. The precise location in which the particle is located depends of the balance of gravitational and dielectrophoretic forces.

Figure 10A:
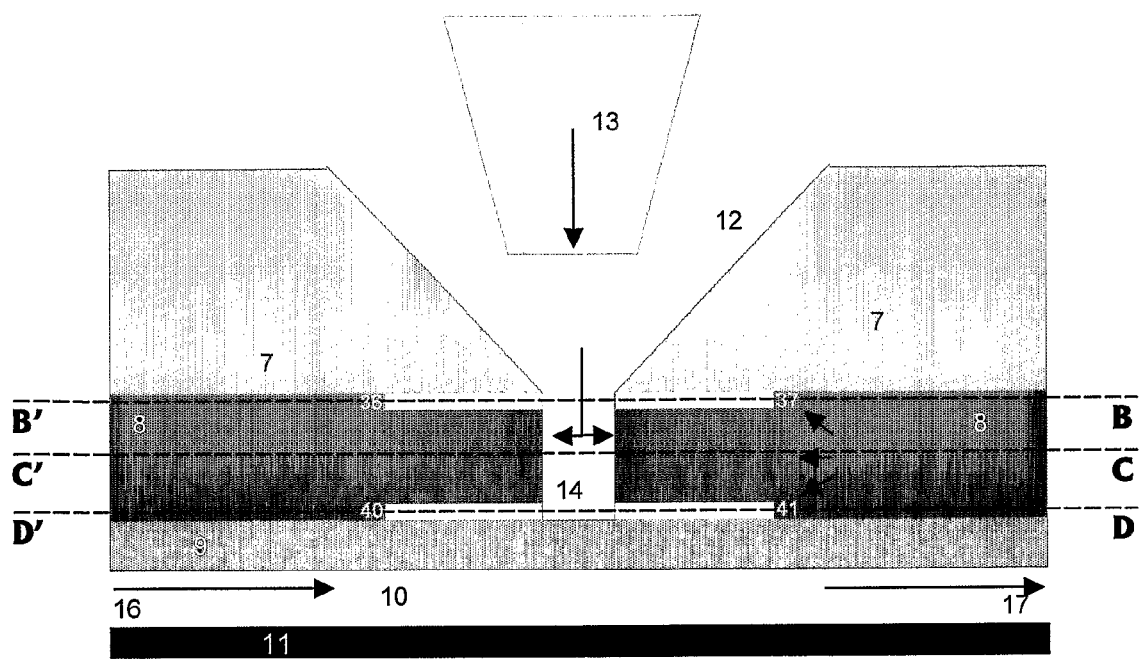
FIG. 10a: shows a section, indicated by A-A' in the following figures from 10b to 10d, through a well according to a further embodiment of the present invention, in the configuration with horseshoe electrodes.
Figure 10B:
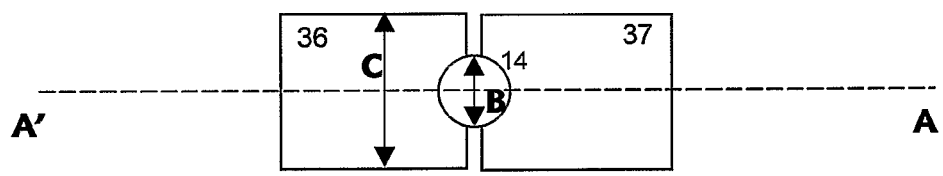
Figure 10C:
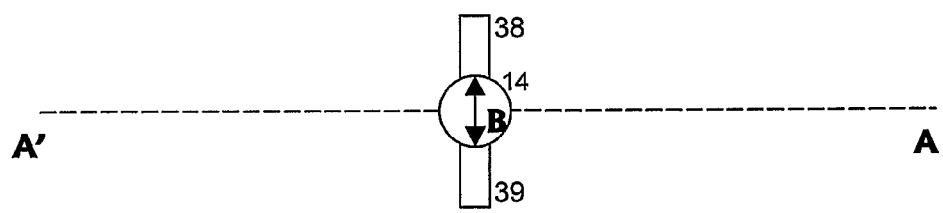
Figure 10D:
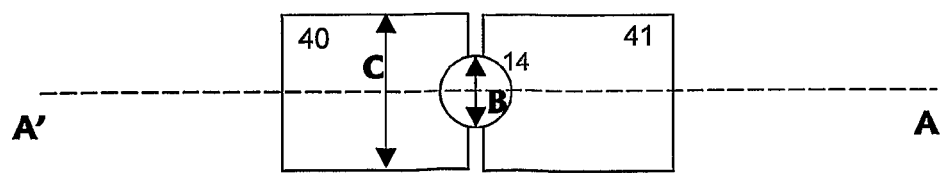

A configuration of electrodes able to position the particle in the well in a very precise region is obtained by making a structure as that shown in FIG. 10*a*, 10*b*, 10*c*, and 10*d*. In this case the upper electrodes 36 and 37 are electrically separated in a similar manner to the lower electrodes 40 and 41, constructed like the lower electrodes 34 and 35 in FIG. 8*a*, hence different voltages can be applied to the two electrodes. Said electrodes are represented in FIGS. 10*b* and 10*d* which show sections along the axes B-B' and D-D' defined in FIG. 10*a*. Preferably, the structure also possesses a pair of electrodes 38 and 39 positioned along an axis perpendicular to the axis of the well and parallel to a surface of separation of the electrode pairs 37 and 37, and 40 and 41. Said electrodes are shown in FIG. 10*c* which represents a section along the axis C-C' defined in FIG. 10*a*.

Figure 11:
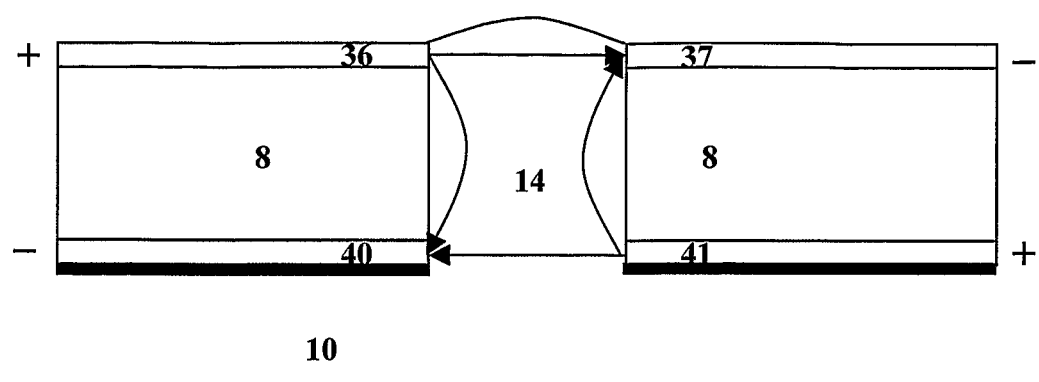
FIG. 11: shows the pattern of the electric field along the section A-A' of a well constructed as shown in FIG. 10 in the case in which the potentials applied to the electrodes 36-41 are in, phase as are the potentials applied to the electrodes 37-40; in this case the potentials applied to the pairs 36-41 and 37-40 are displaced in phase by 180 degrees.
Figure 12:
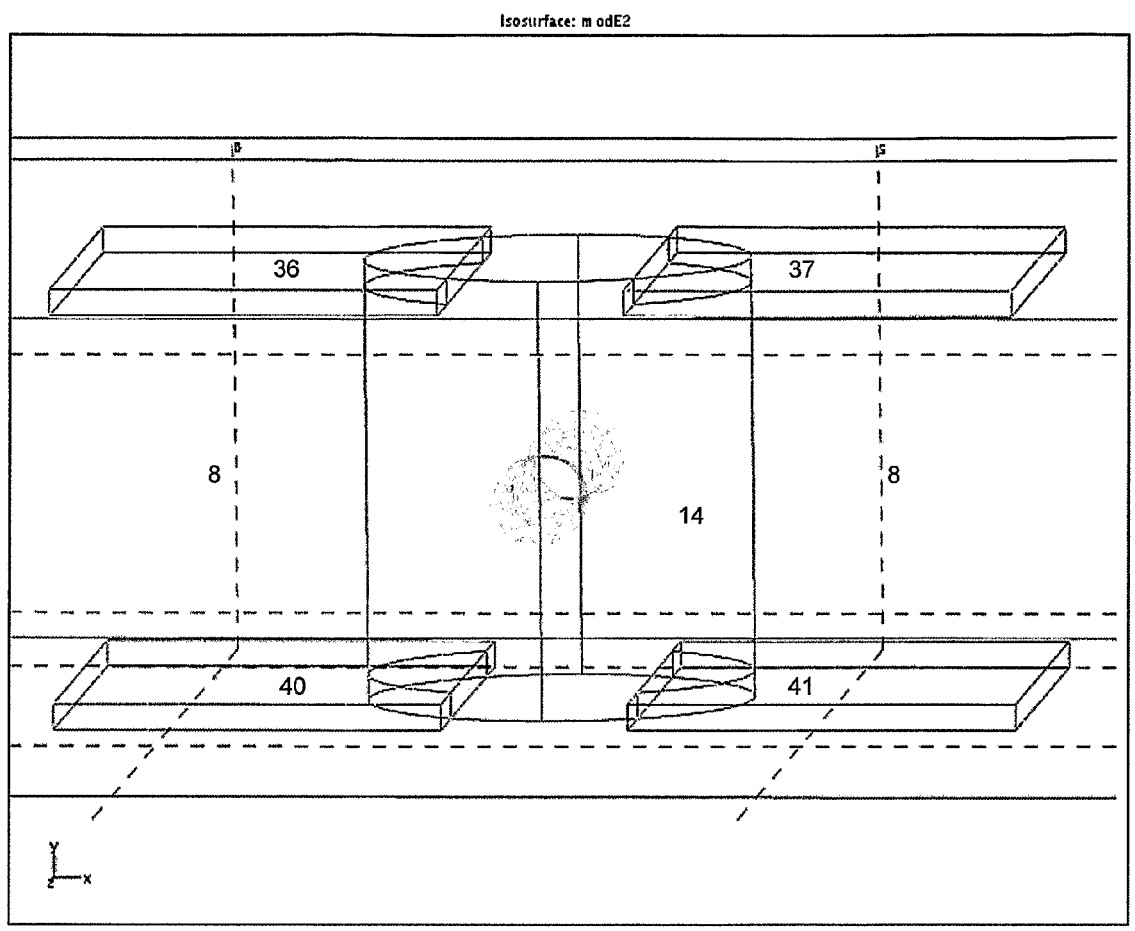
FIG. 12: shows a constant field surface for a well of structure illustrated in FIG. 10 and polarization voltages described in FIG. 11. The surface identifies the minimum region of the electric field which determines a "dielectrophoretic cage".

By choosing now to apply a pair of sinusoidal voltages to 36 and 37 having a mean value of zero, equal amplitude and in mutual counterphase, the phase and amplitude of the voltage applied to 36 being the same as those applied to 41 and those of the voltage applied to 37 being the same as those applied to 40, examination of FIG. 11 enables a possible operating method of the device to be clarified. The section shown in FIG. 11 is situated along the axis A-A' of FIGS. 10*b*, 10*c*, and 10*d*. For the applications of interest the distances between those regions of the electrodes 36 and 40, 36 and 37, and 37 and 41 in contact with the fluid can be the same, even though other possible embodiments can in any case be adopted depending on requirements. The electric field has the pattern illustrated by arrows shown in the figure. In particular, it is high in the region in which the electrode pairs 36, 37 and 40, 41 face each other. As the distance between 36, 40 and 37, 41 is the same as the distance between 36, 37 and 40, 41, a significant electric field also exists between these two latter regions. The nearer to the central region, the more the field lines cancel each other, hence reducing the intensity of the field itself and creating a zero value of the field modulus at the central point of the well. For reasons of symmetry, the electric field modulus along the transverse axis at the section illustrated in FIG. 11 and passing through the central point of the structure, is zero. This effect is evident in FIG. 12, where a surface 102 is present at the intensity of the constant electric field (alternating) obtained as a result of a physical simulation undertaken on the previously described structure. In recollection of the aforesaid, this region is therefore characterized by a field configuration able to entrap particles present inside the well.

By varying the field modulus it can be noted that the intensity of the dielectrophoretic force applied to the particle varies. For example, assuming the presence of a particle having a specific weight greater than water and hence having a tendency to sink in the well, the voltages applied to the electrodes 40 and 41 can be modulated, while the voltages applied to 36 and 37 are for example zero (or constant), so that, if said amplitude variation is slow compared to the time constants of particle motion in a viscous fluid, the particle moves linearly with alternating motion in a vertical direction within the well. This observation has considerable significance for sensor applications which will be illustrated below.

Based on the above, a central region can therefore be created within the device where the electric field modulus is zero, or, by modulating the voltages, where the particles subjected to dielectrophoresis and gravity tend to position themselves. This region has a length equal to the internal diameter of the well 14 and is perpendicular to the plane A-A' in the intermediate region of the well 14.

Figure 13:
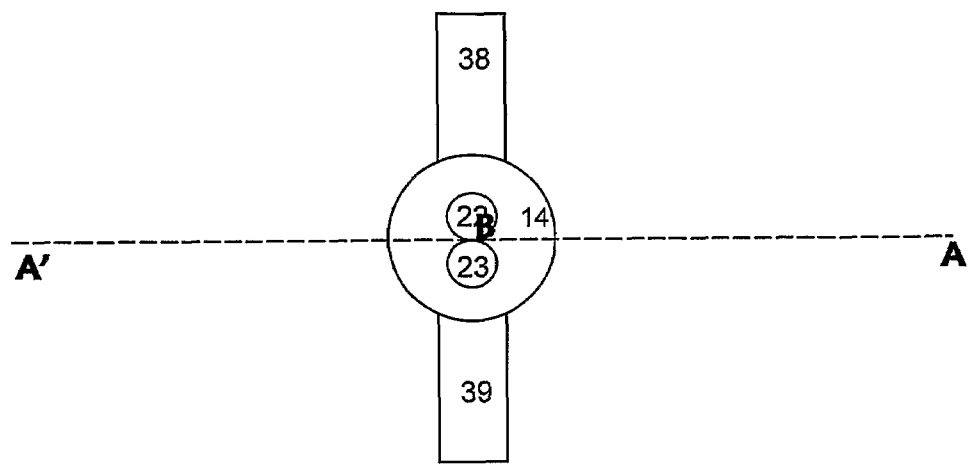

In many cases it is useful to consider how closed cages can be created, by this meaning cages which force a contact between particles which are found in the one-dimensional minimum field region as above. To obtain this result a more sophisticated model of the field in the well can be developed, which shows how the electric field is configured in a way as to create two regions able to attract particles that are located near the electrodes 38 and 39, if these are kept earthed. Firstly, let us examine the case in which particles are required not to lie in contact with the electrodes 38 and 39 to avoid for example adhesion phenomena. To do this, we can examine the case illustrated in FIG. 13. Surmising that the two particles 22 and 23 subjected to negative dielectrophoresis have been inserted into the well and trapped within it in the minimum region of the field, their location is approximately that shown in FIG. 13. Let us now assume for simplicity that the force of gravity does not lower by much the level at which said particles are found and that they remain in a vertical position aligned with the electrodes 38 and 39 which have been constructed to be aligned with the electric field minimum line and are perpendicular to the plane A-A'. Operations which involve the use of the electrode pair 38 and 39 require the application of sinusoidal voltages thereto. Let us assume that a zero mean value is chosen for these voltages and a phase equal to 90 and 270 degrees respectively for that applied to the electrode 38 and 39, with reference to the phase at electrode 36. If the peak potential difference between 38 and 39 is less than that applied between 36 and 37 and between 40 and 41, for example a tenth of the other, the field configuration having a minimum along the central axis is substantially preserved. The field induced instead by the electrodes 38 and 39 has a significant effect on the cells 22 and 23 which normally have a dielectric constant and electrical conductivity of less value than of the surrounding fluid and hence are found in a negative dielectrophoresis situation. Under these conditions and by virtue of the almost spherical shape of the cells in suspension, the cells 22 and 23 behave like lenses which diverge the electric field. This means that for example the cell 22 creates an electric field increase in the region between 22 and the electrode 38, while 23 does the same in the region between 23 and electrode 39. For the same reason, 22 reduces the field intensity in the region opposite 38, and 23 in the region opposite 39. These relative minima and maxima of electric field intensity have the effect of propelling the two cells into close proximity until they touch. It is clear that the force required to achieve this objective is very small as it does not have to counteract other forces such as gravity. Under these conditions it is therefore possible to produce a contact between cells and/or other objects and to keep them in contact with each other. In addition, the alignment of the cells with the measurement electrodes locates them in a favourable position for the measurement itself.

Figure 14:
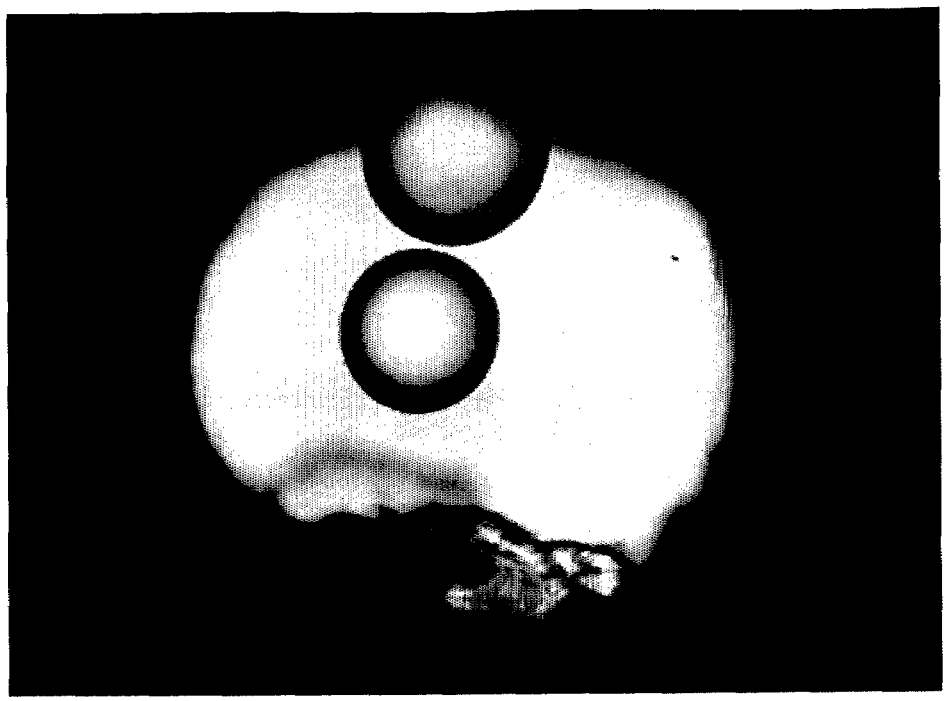
FIG. 14: shows the image of two polystyrene spheres of 90 micron diameter inserted into a well of diameter 300 micron which align themselves in a radial direction as a consequence of activation of the polarization voltages on the electrodes 38 and 39. The reference structure is that given in FIGS. 10a and 10c.

An alternative to the preceding configuration is obtained by polarizing only one of the electrodes 38 and 39, leaving the other earthed. In this case, the particles introduced into the well approach the earthed electrode and align themselves mutually along the field minimum. A configuration of this type is shown in FIG. 14 where two polystyrene spheres have been aligned near to the earthed electrode.

A detailed treatise of these matters is found in the book by H. Morgan and N. Green, AC Electrokinetics: colloids and nanoparticles", 2003, Research Studies Press, Baldock, England, pp. 59-62.

Let us now see how the device of the present invention can be used as a sensor. Referring to the structure described in FIG. 1, experts of the art recognize that the flow of current between the upper circular electrode 1 and lower one 3 is modulated by the possible presence of particles entrapped by the central electrode 2. The situation is similar to that created when a Coulter counter is used which enables particles, such as cells, to be counted with a high degree of precision. In this embodiment, the purpose of the counter is to measure, for example, a variation in the number of particles within the well. A result of this kind in macroscopic wells can be obtained with techniques similar to those of the Coulter counter as described in the work by Thielecke et al. already mentioned. In all these schemes, an excitation signal is connected to electrode 1, while electrodes 2 and 3 can be used as sensors, with the aim of introducing a known voltage or current in the wells and measuring the combined electrical quantity.

The ability to undertake a measurement on the two electrodes 2 and 3 proves to be of particular interest if combined with the motion of the particle along the vertical axis, allowing a measurement that varies with the position of the particle. Simultaneous measurements at different frequencies are also possible, for example at two distinct frequencies, should a suitable signal be applied via electrode 1.

Referring now to the structure in FIG. 10, the integrated actuators formed by the electrodes 36, 37, 40 and 41 are constructed on planes between which another plane is located in which the electrodes 38 and 39 are found. These electrodes, other than allowing the particles to be precisely positioned as previously discussed, can be used for a further task, that of measuring the impedance that exists between them. For this they can also be defined as measurement electrodes, even though they can be used, if desired, for positioning as seen above. As particles of biological interest have a substantial capacitance difference, and in some cases resistance difference, compared with the surrounding medium, the presence or absence of a particle modifies the total impedance observed between the two electrodes. The measurement can be more precise by also measuring the type of cell found between the electrodes, for example by adapting the teachings of Sohn et al., PNAS, Sep. 26, 2000, Vol. 97, to the well of the present invention. An innovative embodiment of the present invention is linked to the fact that the alignment of the particles in front of the electrodes 38 and 39 is essential to maximize the signal/noise ratio obtained during measurement. The ability to move the particle within a well allows it to be placed in a position in which the impedance variation is maximum. A further innovative embodiment of the present invention is the capacity it offers for measuring particles several times while they are in motion, displaced by the variation in voltage amplitude applied to the terminals or by the random motion induced by the fluid subjected to thermal fluctuations. Displacement of the particle induces a variation in impedance over time. If said value can be sampled several times in different positions, the impedance value can be determined by evaluating key parameters such as the maximum value that it acquires over time, with the aim of attaining a precise positioning of the particles between the electrodes 38 and 39.

The sensor hence consists of conductive electrodes 38 and 39, which preferably have a width substantially less than that of the electrodes serving as actuators 36, 37, 40 and 41. A valid dimensioning of the geometries of the electrodes 38 and 39 is such as to give these a thickness of the order of the diameter of the particles to be monitored and a width of between 2 and 10 times the diameter of the particles. In this range it is therefore expedient to consider the fact that the electric field generated by the actuators (manipulation electrodes) is modified by the sensors to which a far smaller voltage is applied than that applied to the other electrodes. Assuming, as a first approximation, that the sensors are modelled as a mass, then the electric field has zero modulus in the regions located in front of it. Although this is a variation of modest spatial extent, it reinforces the electric field minimum situated in the central region of the structure with respect to the surrounding regions and hence contributes to increasing the entrapping capability of the structure. The quality of the measurement is influenced by the capacitive couplings which link the measurement electrodes to those necessary for the actuation. The noise produced by the time-variable voltages on the electrodes used for the actuation must hence be eliminated before the desired signal is read. Possible techniques are the following: frequency-filtering the noise or switching off the actuation electrodes while impedance is being read.

In the first case, use is made of the fact that the oscillation applied for the actuation can have a different frequency from that used for reading the impedance. In this case, experts of the art know that a pass-band filter having an adequate rejection value for the undesired frequency strongly reduces coupling. Another technique uses the concept of measurement in the presence of particles in motion. In this case the procedure is organized as follows: 1) the actuation electrodes 36, 37, 40 and 41 apply a voltage able to locate the particle in a position above that of the measurement electrodes 38 and 39; 2) the actuation electrodes are fixed at a reference potential or earth potential; 3) the measurement electrodes 38 and 39 continuously measure over time the impedance between the electrodes themselves. As the force of gravity moves the particles downwards, the most common case being that they are heavier than the liquid containing them, the impedance measurement sees a first stage in which the particle is above the sensors, a second during which the particle is positioned in front of the sensors and a last during which the particle overtakes them, moving downwards. A quantity of data can therefore be gathered which can be utilized as the dynamics with which the particles move are known.

Matrix Organization

We shall see in the following description how the device works as an array of sensors and actuators.

Considering a platform organized in the form of a matrix the elements of which are wells structured as annular electrodes, as shown in FIG. 1, in the case in which a selective release, from a part of the wells, of particles contained therein is required, the procedure can be as follows: a) the electrode 1 is formed as a uniform structure which provides electrical continuity to all the upper electrodes of the array of wells or as an assembly of separate metal strips parallel to those used for forming the electrode 3; the electrodes 2 and 3 are formed as an assembly of electrically separate metal strips enabling different potentials to be applied to each of them; the metal strips by which the electrodes 2 are formed are perpendicular to those used for forming the electrodes 3; in the description to follow it is assumed that the electrodes 2 are column-connected and the electrodes 3 are row-connected; b) after having carried out the previously described procedure for depositing and entrapping a particle in a well, the sinusoidal voltages applied to the electrodes 3 and 1 have equal amplitude and phase, while those applied to electrode 2 have equal amplitude and are in counterphase; c) having identified a well with x, y row and column co-ordinates in a two-dimensional array, a phase rotation of +90 degrees is introduced to the electrode 3 of row x and a rotation of −90 degrees to the electrode 2 of row y, increasing the amplitude of sinusoidal voltages by about 30% compared to the preceding case. This protocol introduces the following field configuration in the various wells: a) well x, y has a zero field between the electrodes 2 and 3; this eliminates the dielectrophoretic minimum and allows the particle to fall by gravity; b) the remaining wells along row x have a reduced dielectrophoretic force intensity due to the 90 degree reduction in phase difference now introduced between the electrodes 2 and 3; this reduction is compensated by the increased amplitude of the voltage applied to the electrodes; c) the wells along column y have a reduced dielectrophoretic force intensity due to the 90 degrees reduction in phase difference now introduced between the electrodes 1 and 2 and between the electrodes 2 and 3; this reduction is compensated by the increased amplitude of the voltage applied to the electrodes; d) for the other wells in the array there is no change.

Operating schemes for the well structures in accordance with the other embodiments of the invention described can be processed by an expert of the art.

Figure 15:
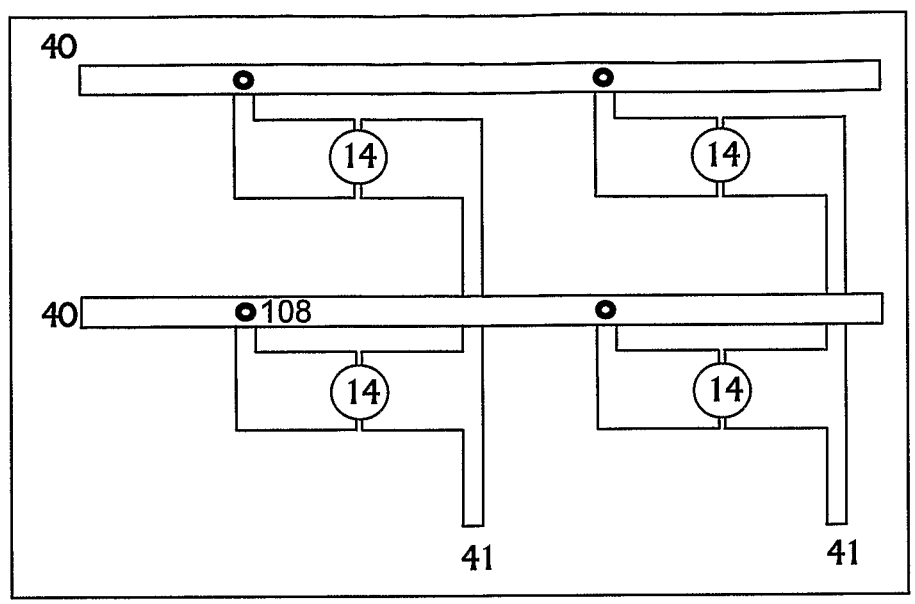
FIG. 15: shows the organization of an array of electrodes in a platform according to the present invention.
Figure 16:
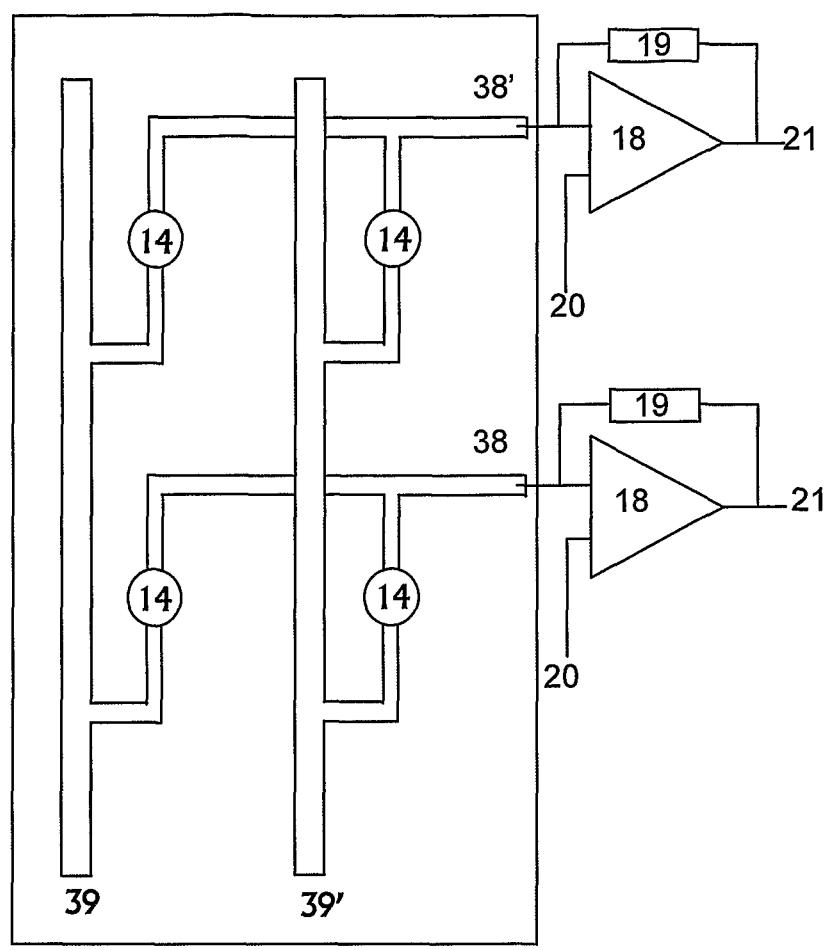
FIG. 16. shows the organization of an array of electrodes, in particular measurement electrodes (also known as sensors), in a platform according to the present invention.
Figure 17:
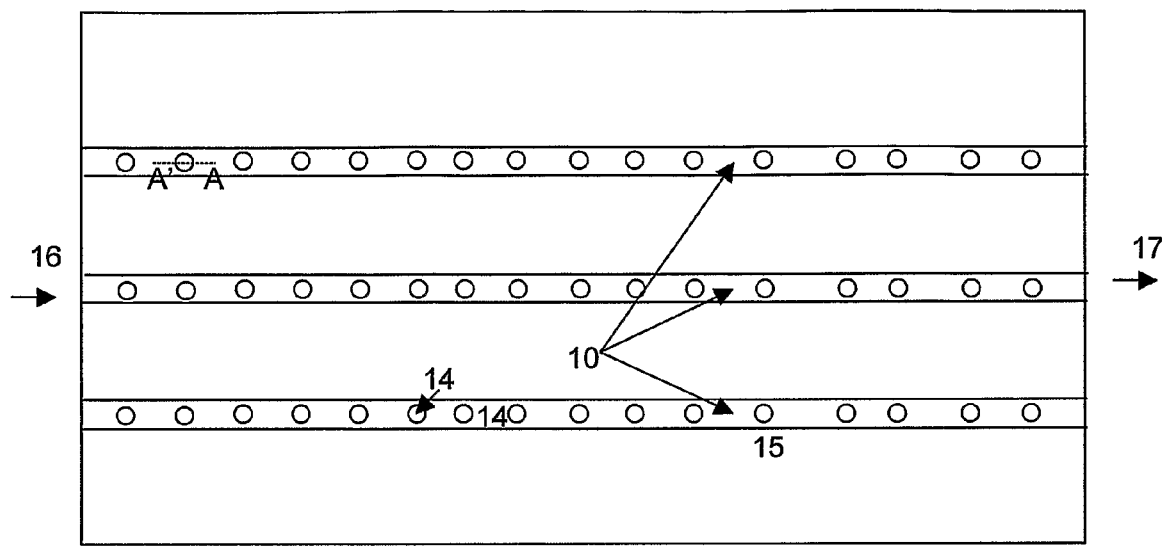
FIG. 17: view from above showing an embodiment of the channels 10 within which the fluid feeding the wells 14 of the preceding figures can flow in a controlled manner.

The organisation of a multiplicity of devices of the type shown in FIG. 10a is easily obtainable as shown in FIG. 16 for sensors and in FIG. 15 for some of the actuators.

Focussing on the organization of the sensors, the operation of an array as that shown in FIG. 16, which represents the plane containing the electrodes 38 and 39, is interpreted as follows. The electrodes 39, 39', 38 and 38' show the situation of an array which comprises 4 wells. An immediate generalization can be made should there be a greater number of wells. Now imagine that a sinusoidal voltage is applied to electrode 39 while electrode 39' remains connected to a reference voltage equal to that applied to 20. Under this condition, two operational amplifiers 18 with non-inverting input 20 connected to a reference voltage, are connected to electrodes 38 and 38'. The retroaction exerted by way of the impedance 19, for example in the form of a resistance, forces the voltage on 38 and 38' to have the same value as the reference voltage applied to 20. The current that flows through 19 to hold the voltages constant as previously described causes a drop in the voltage across the impedance 19 and hence a variation in voltage at the output 21 of the amplifier. If only one electrode 39 is stimulated, the current absorption required by a column 38 or 38' is due to the required absorption of the current that flows through the wells stimulated by the voltage applied to 39, while all the other wells have no potential reduction across the electrode pairs 39'-38 and 39'-38' which are equipotential. In this manner the impedance which is created between each well can be controlled by scanning the array in a sequential manner. If necessary it is then possible to repeat scanning in a cyclical manner.

The array-type operation of the device as an actuator is more simple, as shown in FIG. 15 which shows one of the planes on which the electrodes are located, for example 40 and 41. In particular, well loading with particles and the selective release thereof are the most important steps. The loading step requires that the voltages applied to the upper electrodes 36 and 37 are at zero during particle introduction. This avoids creation of a high field region between the electrodes which would hinder particles from entering the well. Only after the particle has been introduced should the voltages at the electrodes 36 and 37 be reactivated.

The downflow of particles into the outlet channel 10 is controlled in the following manner. Said outlet channel 10 allows the fluid inlets 16 and the fluid outlets 17 to be connected, and to collect the cells or particles possibly released from the wells as aforedescribed. Should all the particles contained in the wells need to be recovered, it suffices to earth the voltages applied to the electrodes 40 and 41 present in all the wells. The force of gravity allows the particles to downflow towards the collection channel. Should the recovery of a precise fraction of the particles be required, we assume for simplicity that only the release of the contents of a single well having coordinates identified by the two numbers i and j is required, associated respectively with the row and column that unequivocally identify the preselected well. The recovery procedure can be organized as follows: 1) all the potentials applied to the electrodes 36 and 37, 38 and 39 are earthed; 2) the voltages applied to the electrodes 40 and 41 undergo a voltage amplitude increase, selected so that the voltage applied is sufficient to prevent the particles from leaving the well even if one of the electrodes 40 or 41 is set to zero amplitude; 3) the voltage associated with the electrode 40 of row i and electrode 41 of column j is set to zero amplitude. This selection enables the following situations to occur: a) wells in which the electrodes 40 and 41 have an associated 0 and 180 phase voltage and an amplitude such as to impede the downflow of the well contents; b) wells along column j and row i, excepting the well i, j; in this case at least one of the electrodes 40 or 41 has an associated voltage of amplitude such that downflow of well contents is prevented; c) the well i, j is the only one to have both the afferent electrodes 40 and 41 with their associated voltage of zero amplitude. By repeating this procedure for all the wells of interest, the required contents of a fraction of the available wells can be recovered, by making the contents fall into the channel 10 and transporting it towards the exit end 17.

If information on the location where cells were released is not required, the flow of the fluid itself allows the material to be transported. In the case where precise information about the location of the well from which the material was released is required, it is possible remove the material contained in the well by suction using simple fluid apparatus.

Controlling Particle Position by Means of Dielectrophoresis and Evaporation

The intensity of the dielectrophoretic force is imposed by its opposition to the force of gravity. The structure of the well with an open upper orifice enables possible evaporation of liquid to be synergistically used to reduce the required dielectrophoretic force intensity, hence reducing the electric fields required and dissipation of power in the fluid. The microfluidic control of particles has been reported in the literature in a number of fields. By way of example, reference can be made to a work which appeared in Lab on a Chip, 2005, pp. 1355-1359, documenting how the controlled flow of a fluid can be used to move particles. The need for carrying out precise displacements requires complex temperature control structures which cannot be easily generalized by arrays such as those described in the present application.

Again, by way, of example, minute water droplets which form on hydrophilic or hydrophobic surfaces have different forms. Now consider FIG. 1, demonstrating the presence of a liquid which creates a meniscus 30. Said mechanism is documented by FIG. 2 for an array of. wells. The surface 30 can be exposed to an air current, possibly forced by a suitable mechanism which induces evaporation of the liquid. Evaporation causes an upward motion of the fluid in the well, producing a motion counteracting that induced by the force of gravity. In particular, the liquid flow velocity required to completely counteract the force of gravity must be equal to the descent velocity of the particle. For example, for a eukaryotic cell immersed in water, the descent velocity is in the order of 10 microns per second. A flow of equal and opposite velocity which flows into a well 14 having a 50 micron diameter in the region where the electrodes are present gives rise to a fluid flow rate of 1 nL/minute. If the form of the well in the region above where the electrodes are sited shows a rapid increase in diameter up to 1 mm in the upper part and if the hydrophobic treatment is applied only to the external surface of the platform and not to the internal walls of the well and the walls 12 of the upper part 7, a meniscus forms on the surface where the diameter of the hole is greatest and equal to about 1 mm. To favour this, in accordance with a possible embodiment of the invention, the walls 12 and the internal walls 103 of the well can have, in contrast to that envisaged in a previously discussed embodiment of the invention, equal hydrophilic or hydrophobic characteristics. The evaporation needed to balance the required flow rate is then compatible with that obtainable by a current of air in forced convection with a jump in temperature of 7K relative to the dew point. Under the conditions just described, it is clear that controlling the position of the particle is imprecise if the flow of fluid were to be the only way of controlling the particle. Instead, by combining technology based on dielectrophoretic principles with that involving fluid evaporation, a useful synergy is gained between the precision offered by the first and the reduction in the electric fields made possible by the second method. A theoretical model and the experimental results relative to this approach are documented in the work "An Integrated Electronic Meniscus Sensor for Measurement of Evaporative Flow" which will be presented at the conference Transducers 2007, in Grenoble, France.

Applications of the Described Well-Based Apparatus in the Field of Biology

The movement of a single cell in parallel wells, as well as the ability to modify the culturing conditions in the individual wells, allow for a number of applications, some of which will be described in detail in the following. The potential applications of the apparatus are amplified by the feasibility of integrating the dielectrophoretic movement with different bioanalytical methods, through the use of various sensors.

The apparatus can also comprise suitable methods for separating and/or selecting particles.

In a preferred embodiment the sensors are measurement electrodes and in particular measure the impedance of the well and its contents. By virtue of different cell behaviour in an electric field and the relative impedimetric measurement, results that are important in the biological field have already been obtained, such as the separation of cancerous cells from blood (Becker F. PNAS, 1995, 92:86).

In this regard it has been observed that the capacitance and conductivity of biological membranes change following cell activation (Hu et al. Biochim, Biophys. Acta, 1991, 1021: 191) and that they differ, one cell-type from another. These form the bases for selection protocols applied to single cells or to a few cells in an individual well, with the apparatus described. By measuring impedance characteristics or variations, it is also possible to measure the lipid content of cells, cytoplasm or culture medium, and the condition of the membranes, due to activation, in single cells, of lipid production (Biotechnology & Bioengineering, 1999, 65:537-541) or of other molecules which modify the impedance.

Biological characteristics relating to the lipid content of the culture medium or the cell, obtainable by impedimetric measurements, are those in which the state of the membrane is altered or damaged as occurs during cell lysis, by necrosis or apoptosis, due for example to cytoxicity phenomena, which hence becomes detectable in an individual well.

Impedimetric and/or optical measurements allow the measurement of cell amplification following cell duplication and therefore the stimulatory conditions which induce amplification as a cellular response.

In accordance with another preferred embodiment, the sensors integrated in the dielectrophoretic motion and/or confinement system are of the optical type and indicate luminescence, fluorescence or optical density at different wavelengths.

By measuring fluorescence as an optical signal, calcium fluxes can be detected, induced for example by receptor activation or by interaction with secondary cellular messengers, even when induced following changes in growth conditions. These cellular responses therefore become measurable on single cells and in parallel on individual wells. Cell lysis phenomena can be perceived as fluorescence signals in cases where the particles have been loaded with fluorophores or chromophores which are released in the medium only after lysis or alteration in cell permeability.

Optical and/or dielectric signals correlate with cell morphology changes, following for example stimuli for cell adhesion or migration or serious alterations of membrane properties due to lysis, programmed death (apoptosis) or cytotoxicity, which can therefore be identified and precisely correlated to known stimuli in the culture.

Sensors suitable for impedimetric and optical measurement are hence able to identify morphological, chemical, biochemical or metabolic characteristics of the particle or medium.

Application to Modification of Cell DNA

Modifications to the genetic material of cells are achieved preferably by electroporation or cell fusion. In this case the particles are biological particles, such as microorganisms, comprising eukaryotic cells, yeast or bacteria, or fragments thereof or small aggregates thereof or derivatives, such as protoplasts. However, the method also applies to biochemical particles mainly consisting of lipids or phospholipids, such as liposomes.

We shall now examine how the device of the present invention functions as a cell electroporator and modifier. The reference structure used in the description that follows is that shown in FIG. 10. The availability of an array of wells within which is assigned the capacity to effect particle motion and the measurement of particle characteristics enables the creation of an efficient electroporator which can work in parallel on a multitude of single cells. As was understood from the preceding description of its operation, the device allows numerous manipulations to be effected which are essential for this protocol. In particular, it is possible to locate the microorganisms in front of measurement electrodes 38 and 39 and to be assured of this by measuring impedance. Downstream of these measurements the same electrodes can be used to force voltages of the required magnitude to achieve electroporation, as described for example in Khine M. et al. Lab Chip, 2005, 5, 38-43. The potential pulses can be of a lower intensity than that normally used in conventional electroporators. This is due to the fact that the electroporation takes place in a chamber of a suitable size for containing one or few cells. The reduced size enables a significant field to be obtained even with modest shifts in potential. These suitably applied potentials create temporary pores in the cell membrane and allow species in the supernatant, present at higher concentrations than found in the cytoplasm, to migrate into the cell itself.

Of particular use is the possibility of changing the supernatant within which the microorganism is located. It is known that electroporation requires supernatants characterized by low conductivity to avoid excessive passage of current and hence excessive heating of the biological material. These supernatants are however poorly suited to host the microorganism for extended periods following electroporation. It is therefore normal practice to remove microorganisms from the chamber within which the procedure takes place and to move them into a more suitable environment to overcome the critical phase during which the membrane repairs. This procedure is difficult to undertake when dealing with only a few cells and, in addition, displacement of microorganisms tends to disturb them during this delicate phase. The proposed solution in this patent resolves this problem, in that the supernatant can change while the microorganism remains in a stable location, maintained in situ by the dielectrophoretic cages. To schematically summarize the various passages, the starting point is the stage in which the supernatant consists of. physiological solution for maintaining the microorganism in optimum conditions. The preceding supernatant is substituted with a solution of low conductivity. During this stage the position of the particles can be controlled by the procedure described previously involving actuators. Following electroporation, the low conductivity supernatant can be removed or substituted, placing the microorganism in optimum conditions for reconstructing the damaged membrane without having to move it, by substituting the growth medium. Genetic modifications can be achieved with the described mechanisms, by introducing exogenous DNA by electroporation or by fusion of two genomes. Electroporation, can also be undertaken in the presence of exogenous substances other than DNA, for example drugs or macromolecules unable to cross the cell membrane.

Another very important protocol for modifying the genetic material of microorganisms is electrofusion, carried out for example as described in US2003/0104588. In this case, the previously described procedure does not change, but uses the deposition of. different types of single cells inside the chamber creating a great number of fusions between cells, in parallel. In particular, as widely described in the literature, for large numbers of cells or bacteria, a cell aggregate is created to which a potential is applied able to facilitate fusion of microorganisms suitably treated to facilitate DNA exchange. In the case of bacteria, the organisms are treated in such a way that the membrane loses its protective layer. The protoplasts thus obtained are placed in contact with each other applying the potentials described in the section dedicated to actuators and creating a dielectrophoretic force which forces the protoplasts to remain in the same spatial region.

The possibilities known to the skilled artisan for obtaining or improving efficiency of fusion between particles or cells in the presence of an electric potential generated as described above, or even in its absence, with a simple approach, comprise the use of chemical compounds which facilitate fusion (e.g. polyethylene glycol, polybrene, DEAE-dextran, Fycoll) according to known protocols (see for example fusion for preparing hybridomas and/or fusion of protoplasts). Adhesion between cells can be obtained in an environment characterized by a lower osmolarity than usual. For example the protocol described in Applied and Environmental Microbiology 2004, p. 2391-2397 describes steps wherein the cells to be fused are exposed to different compounds. In particular, fusion takes place by remixing the solution containing the cells so as to favour their contact and, thereafter, adhesion. In the case described in this document, adhesion is achieved by virtue of the thrust exerted by the dielectrophoretic force.

Other protocols achieve cell fusion by the application of a suitable voltage (electrofusion). The procedure is completed by allowing the surviving microorganisms or cells to reconstruct their membranes and to recover vital functions which were damaged by the previously described step by modifying the culturing conditions of the cells subjected to electroporation or cell fusion. Said option was demonstrated by an experiment organized as follows: a) the wells are filled with a fluid of a conductivity equal to that of physiological fluid; b) the installed sensors measure conductivity of the liquid; c) a liquid with a lower conductivity and suitable for undertaking electroporation is introduced into the channel 10; d) the conductivity of the new fluid is measured. The results of this experiment are shown in FIG. 18 where it can be seen that the supply of a controlled fluid flow allows the supernatant in the wells to be modified with precision. In particular, it can be seen that by simple measurements of the real part of the impedance between the electrodes 36 and 37, it is possible to distinguish between a well with no liquid inside, one in which a low conductivity solution has been inserted often used as a buffer during protocols for modifying the genetic material of a cell, and one with a high conductivity solution, typical of physiological solution.

This procedure can also be applied to the electroporation procedure. In particular, the ability to change the supernatant at different stages allows introduction of a low conductivity liquid when protoplast fusion is required, a liquid able to remove the membrane protective layer during their preparation stage and finally a liquid containing suitable nutrient compounds during the stage of functional reactivation. As the wells allow all these steps to be carried out at the level of a single cell, the overall procedure does not change when used on a macroscopic scale, hence allowing investments in already available protocols to be retained, while opening new possibilities for organizing protocols in that the outcome of the fusion procedure is very controlled and hence optimization algorithms can be applied which are based on knowledge of the precise interaction between cells which has given a certain type of result.

The aforedescribed procedures give rise to a population of cells which a) have survived the treatment and b) demonstrate different functional characteristics from each other.

The sensors available in the well are fundamental during this stage as: a) survival can be measured by virtue of the fact that the cell mass is growing and hence changes the impedance measured between the electrodes used for the measurement; b) depending on the type of phenotype required, it is sometimes possible to select clones that clearly show a greater expression of said phenotype. By way of example the capacity of a bacterial specimen to produce lipidic substances can be measured by virtue of the fact that the dielectric constant and resistance of lipids is very different from that of the other materials of which a cell consists. In this case for example there is therefore a dependence of the measured impedance on the concentration of lipids.

Application to Cell Selection

The platform of the present patent has an immediate application in the selection of cloned cells based on their selective lytic ability towards suitable target cells. By way of example, some immune system cells belonging to the CTL and NK family exhibit a significant lytic activity towards tumor cells and recognize healthy cells as such. Still unknown is the reason why these cells with a lytic activity are present in reduced numbers in patients and even more important, how these cells of particular interest can be isolated. The problem of functional selection of cells has to be solved, i.e. cells that should be selected not because of the presence of known surface markers but because they show specific functional properties.

The previous explanation allows a selection protocol to be made on this platform based on the availability of apparatuses able to deposit single cells, such as those produced by Daka-Cytomation and by following these steps: 1) the target cells, for example tumor cells, are deposited in wells in known quantities, for example one cell per well; this result requires that the deposited cell be captured by the device; 2) a known quantity of cells having a presumed lytic effect, for example a CTL or NK cell, is deposited in the wells; the voltages remain such as to capture the particles inserted in the wells; 3) by creating a field configuration which forces the surfaces between the cells in the well to interact, the presence of a lytic effect is measured by determining a different impedance with a procedure similar to that previously described; 4) the cells which have demonstrated a lytic effect are recovered and are expanded monoclonally in a conventional container; 5) the procedure described in points 1) to 4) is undertaken to verify if the thus selected cells have a differential effect, i.e. they do not attack undesirable targets, such as healthy cells; 6) the cells are again expanded if selectivity is confirmed. In this case, the platform of the present Application is also useful for verifying and possibly selecting cells during their expansion in vitro. Indeed, it is known that expansion of CTL cells shows a change in the genetic code of some daughter cells after a few reproductive cycles. This is of particular significance when considering that the number of cells selected during the initial stage of the protocol is of the order of a few dozen, whereas the useful quantities from a therapeutic viewpoint require some hundreds of millions of cells. The number of expansion cycles required is greater than that during which the original genetic code is preserved. The problem can be resolved by carrying out a procedure with more selection steps similar to those previously described. By way of example, the cells extracted by means of selection are expanded a first time, then after a suitable number of expansions their functional characteristics are confirmed by repeating the selection procedure. In this way, the number of expansions needed to reach a therapeutic level is reduced and the reproducibility of the functional characteristics of the cells is ensured. The organization just described is achieved by applying a sequence of suitable voltages. In particular, referring to the structure in FIG. 10, during the stages of depositing cells into the wells, the voltages at electrodes 40 and 41 will be activated, while the other electrodes will have a voltage with zero amplitude. This selection allows the well outlet to be closed and the introduction of cells into the well not to be hindered. The interaction stage proceeds as previously described, by applying a suitable voltage to all the electrodes with the aim of forcing their interaction. Any lysis is detected by the sensors provided in the various wells or by optical observation based on the release of suitable dyes which are released when the cells undergo lysis. These observations allow the determination of when and where the cells to be recovered are present.

Figure 19:
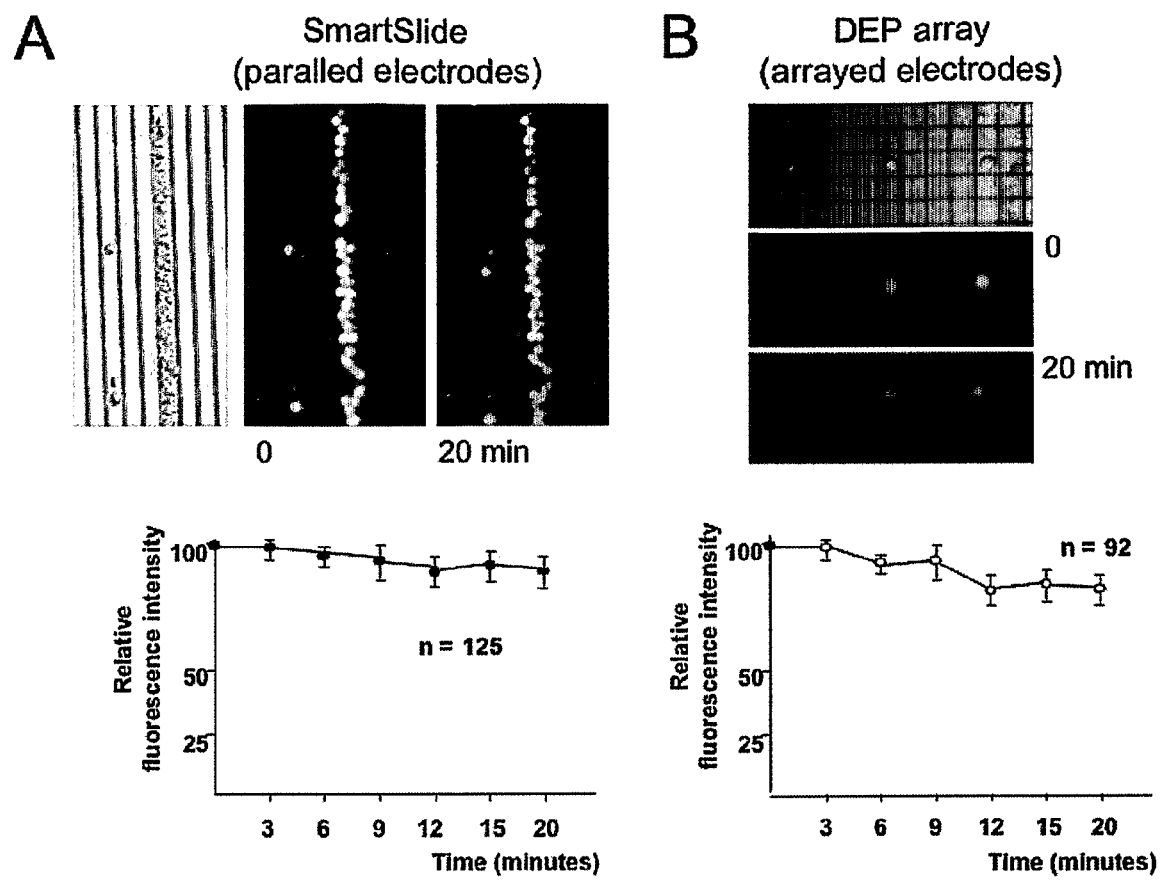
FIG. 19: stability of calcein marker following DEP stimulation. To check, that dielectric treatment does not alter the fluorescent signal, LCLs loaded with calcein were treated at 100 MHz and placed on a SmartSlide and DEP-array: as is shown, fluorescence intensity remains more or less constant over time. The fluorescence signal, measured every minute, is determined from 125 cells in the case of the SmartSlide platform and from 95 cells in the case of the DEP-array platform.
Figure 20:
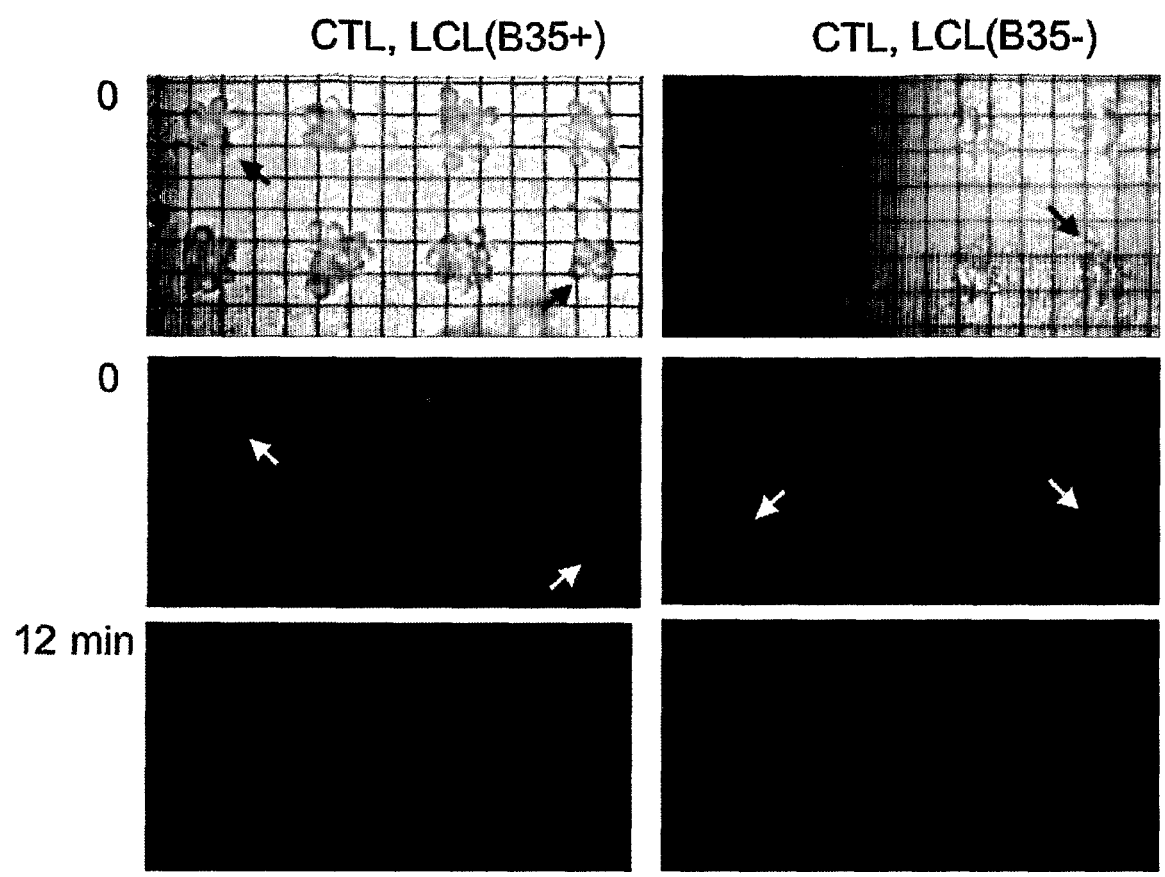
FIG. 20: calcein-labelled LCLs loaded with the peptide EBV (left hand panel) and non-loaded control LCLs were incubated with CTL, activated for 15 minutes. The cell complexes were separated, resuspended in a mannitol buffer and distributed on a DEP array: the fluorescence signal was then measured at time 0 and after 12 minutes: the arrows indicate those cell complexes which do not contain LCL. At time 12 minutes, the fluorescence signal disappears only where specific lysis of LCL has taken place, but not in the control (right hand panel).
Figure 21:
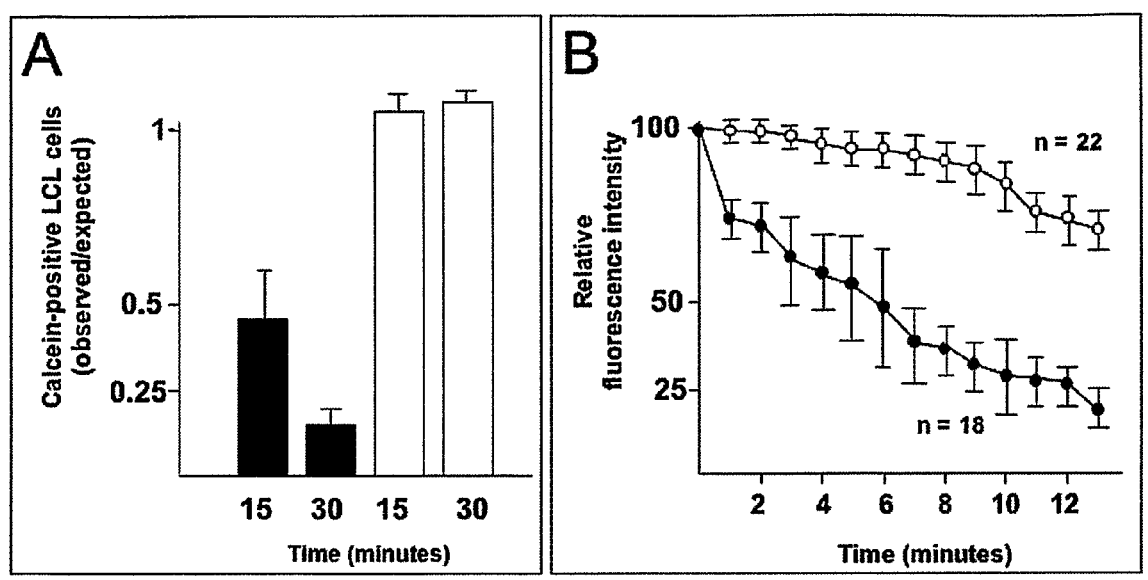
FIG. 21: in panel A the histogram represents fluorescence signal reduction due to lysis of LCL loaded with EBV peptide or not loaded with the peptide, incubated with CTL for 15 minutes and 30 minutes then separated on a DEP-array in mannitol buffer. The histograms in panel A refer to time 0, the curves in panel B refer to the times indicated on the x-axis. In black: lysis of positive LCLs (loaded with the peptide), in white: control (non-loaded LCLs)

A demonstration of the feasibility of the protocol for the functional selection of cells with lytic activity is described in the experiments shown in FIGS. 19-21, achieved with a commercial platform, the DEPArray, produced by Silicon Biosystems S.p.A, Bologna, Italy.

FIG. 19 shows that the DEPArray creates dielectrophoretic cages according to a physical principle analogous to that of the present invention and that the electromagnetic effects are compatible with an optical-type measurement of cellular conditions and in particular with fluorescence measurement after labelling with calcein. A total of 95 cells were placed in a DEPArray, labelled with calcein and exposed for over 20 minutes to electromagnetic fields at 100 MHz amplitude analogous to that required in the present invention. It could be seen that these cells give a measurable fluorescence signal without a reduction in intensity for the whole duration of exposure to the electric field, confirming that under these conditions the are no significant spontaneous lysis phenomena. This also allows functional selection protocols to be applied to cells whose isolation is particularly problematic or poorly efficient, such as stem cells, lymphocytes, specific cytotoxic lymphocytes etc.

The capacity to determine the lytic activity of effector CTLs towards target cells which present tumor antigens, is shown in the experiment of FIG. 20. The experimental context is the following: lymphoblastoid cell lines (LCL) were obtained after infecting human B lymphocytes with the Epstein-Barr Virus (EBV) B95.8 strain (Salter, R. D., and P. Cresswell, 1986, EMBO J. 5:943-949). The EBV-specific peptide HPVGEADYFEY (corresponding to aa 407-417 of the EBNA1 protein) was used for the stimulation. Peripheral blood lymphocytes (PBL) from a HLA-B35 donor were plated out at a concentration of $3.5 \times 10^6$ cells per well in 24-well plates, in RPMI 1640 culture medium with 10% FCS (Hyclone) and stimulated with the HPV peptide (10 µM). The cultures were restimulated after 7 and 14 days and the medium was supplemented with 10 U/ml rIL-2 (Chiron). On days 14 and 21 the T cell cultures were analysed for CTL activity using cytotoxicity canonic assays ($^{51}$Cr-release) (Hillman G G, Roessler N, Fulbright R S, Pontes J E, Haas G P. $^{51}$Cr-release assay adapted to a 96-well format sample reading. Biotechniques. 1993; 15(4):744-9).

In the experiment, whose results are given in FIG. 20, the human lymphoblastoid line infected with the EBV (LCL), further loaded with a EBV peptide (LCL-B35 positive) and labelled with calcein, was incubated with CTLs obtained from PBL (Peripheral Blood Lymphocytes) of peripheral blood depleted of monocytes and stimulated in vitro with an EBV specific peptide (corresponding to aa 407-417 of the EBNA1 protein of EBV) and with IL-2. FIG. 20 shows that the target lymphocytes pre-tested with specific CTLs can be moved by DEP forces and disposed in groups of 4-5 cells, in array format, within the cages corresponding to the different electrodes. After 12 minutes, the cell complexes that contain CTLs, detectable as fluorescent signals, disappear only where there is specific lysis (12 minutes, left hand: panel), made possible by the presence on the target cells of the tumor epitopes (EBV peptide) recognised by the CTLs. The reproducibility of the specific lysis was verified in the experiment shown in FIG. 21, in which the mean of three different experiments is given, carried out as described in FIG. 20. Measurement of the fluorescence signal carried out every 30 seconds in real time indicates that the system established with DEP cages allows specific lysis of the complexes comprising CTL to be determined and that said lysis is clearly shown, with values that can be distinguished from a control ("target" cells not loaded with the peptide) even after 2 minutes.

In accordance with the present invention, it has therefore been demonstrated that a biological activity, such as that of recognition and specific lysis of target lymphocytes by CTLs, is not changed by dielectrophoresis conditions when associated, for example, with a viability labelling method using a fluorescent dye such as calcein, which according to the present invention can be used as an optical signal in dielectrophoresis and is able to measure changes in cell complexes comprising from one to a small number of target cells.

Therefore the present invention relates to the use of the described apparatus for the functional selection of experimental conditions which induce cellular degeneration, for example lysis, apoptosis, necrosis, and where said degeneration can be determined by an optical or electrical signal variation (e.g. impedance) in a buffer or other biocompatible medium. Said method uses a solid support, preferably a microplate, comprising the wells of the invention disposed in series which enables both the movement of cells within a well, for the purposes of cell interaction, and their disposition in the array, as well as the detection of impedance variations within the same well or microchamber.

The present invention therefore offers the following advantages:
a) radioactive labelling of cells for detecting cytolytic reactions is no longer necessary;
b) many groups of cells incubated under the same conditions can be monitored in parallel and offer statistically significant values;
c) the analysis of a single cell is possible and this involves the advantage of being able to use the minimum number of target cells;
d) the protocol is fast and the results can be obtained within a few minutes;
e) measuring changes in cells (e.g. cytolysis) can be undertaken in real time.

According to a preferred embodiment the method is aimed at the selection and amplification of cytotoxic autologous or heterologous lymphocytes or NK, able to recognize and specifically lyse tumor cells, or cells infected with microorganisms, bacteria and/or viruses, or even cells presenting under pathological, conditions, recognizable antigenic and/or functional characteristics compared to normal cells.

The invention claimed is:

1. A structure including at least one microwell and a channel, the at least one microwell comprising:
   a dielectric material forming at least one lateral wall that delimits the at least one microwell and extends between an upper end and a lower end, the at least one microwell open at the upper and open at the lower end, the at least one microwell configured to retain a first volume of a liquid and particles contained within the liquid, such that the first volume of the liquid forms a meniscus at one of the upper end and the lower end when retained in the at least one microwell; and
   at least two manipulation electrodes within the dielectric material such that each manipulation electrode at least partially defines the at least one lateral wall, the manipulation electrodes able to be powered by electrical voltages so as to produce dielectrophoretic manipulation of particles in the at least one microwell;
   wherein the channel includes an inlet and an outlet and is configured to allow at least a second volume of the liquid to flow from the inlet to the outlet, and wherein an axis extending from the inlet to the outlet, along the direction of liquid flow within the channel, is oriented perpendicularly to a central axis of symmetry of the well, the central axis of symmetry extending from the upper end to the lower end, and wherein the channel is in direct fluid communication with the one of the upper end and the lower end of the at least one microwell that is opposite the end at which the meniscus forms, and wherein the channel is configured such that the liquid may flow directly between the channel and the microwell.

2. The structure of claim 1, wherein the meniscus is disposed at the upper end of the at least one microwell, and wherein the channel is disposed at the lower end of the at least one microwell.

3. The structure of claim 1, wherein the manipulation electrodes comprise plates of conducting material substantially disposed in different planes transverse to the central axis of symmetry of the at least one microwell.

4. The structure of claim 1, wherein the manipulation electrodes face each other across a lateral wall delimiting the at least one microwell, the lateral wall comprising a dielectric material in which the manipulation electrodes are embedded.

5. The structure of claim 1, wherein the lateral wall delimiting the at least one microwell has a hydrophilic surface.

6. The structure of claim 1, wherein the lateral wall delimiting the at least one microwell has a hydrophobic surface.

7. The structure of claim 1, wherein a wall external to the at least one microwell and adjacent to the at least one microwell lateral wall has a hydrophilic surface and the at least one microwell lateral wall has a hydrophobic surface; or the wall external to the at least one microwell and adjacent to the at least one microwell lateral wall has a hydrophobic surface and the at least one microwell lateral wall has a hydrophilic surface.

8. The structure of claim 1, wherein at least one of the manipulation electrodes forms an annular rim along the delimiting wall of the at least one microwell, the rim being disposed substantially in a plane transverse to the central axis of symmetry of the at least one microwell.

9. The structure of claim 8, wherein the at least one microwell includes at least three electrodes disposed in parallel planes, forming the annular rim.

10. The structure of claim 1, further comprising at least one pair of electrodes disposed in the same plane transverse to the central axis of symmetry of the at least one microwell, forming two annular rim portions along the delimiting wall of the at least one microwell separated from each other by a surface parallel to the central axis of symmetry of the at least one microwell.

11. The structure of claim 10, further comprising an electrode forming a second annular rim disposed in a different transverse plane than the pair of electrodes, the second annular rim disposed towards the upper end of the at least one microwell with respect to the pair of electrodes.

12. The structure of claim 10, comprising two pairs of electrodes disposed in two different planes transverse to the central axis of symmetry of the at least one microwell.

13. The structure of claim 1, further comprising sensors for measuring physical and/or chemical characteristics of at least one microwell contents, wherein the sensors are of impedimetric, optical or potentiometric type.

14. The structure of claim 13 wherein the sensors of impedimetric type comprise a pair of measurement electrodes configured to measure impedance, the measurement electrodes suitable for displacing particles contained in the at least one microwell and/or to induce electroporation or fusion reactions if suitably powered.

15. The structure of claim 1, wherein the meniscus is disposed at the lower end of the at least one microwell, and wherein the channel is disposed at the upper end of the at least one microwell.

16. The structure of claim 1, wherein at least one of the manipulation electrodes is able to also function as a sensor.

17. The structure of claim 1 comprising a plurality of channels, each of the channels coupled to a plurality of microwells.

* * * * *